(12) United States Patent
Goggins et al.

(10) Patent No.: US 7,153,653 B2
(45) Date of Patent: Dec. 26, 2006

(54) DIFFERENTIALLY METHYLATED SEQUENCES IN PANCREATIC CANCER

(75) Inventors: Michael G. Goggins, Baltimore, MD (US); Takashi Ueki, Sparks, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 619 days.

(21) Appl. No.: 10/084,555

(22) Filed: Feb. 25, 2002

(65) Prior Publication Data

US 2003/0190616 A1    Oct. 9, 2003

Related U.S. Application Data

(60) Provisional application No. 60/271,268, filed on Feb. 23, 2001.

(51) Int. Cl.
*C12Q 1/68* (2006.01)
(52) U.S. Cl. .......................................................... 435/6
(58) Field of Classification Search .................. 435/6, 435/91.1, 91.2; 536/23.1, 24.3, 24.33
See application file for complete search history.

(56) References Cited

U.S. PATENT DOCUMENTS

| 5,552,277 | A | 9/1996 | Nelson et al. .................. 435/6 |
| 5,756,668 | A | 5/1998 | Baylin et al. ................ 530/350 |
| 5,856,094 | A | 1/1999 | Sidransky et al. .............. 435/6 |
| 5,871,917 | A | 2/1999 | Duffy ............................ 435/6 |
| 6,251,594 | B1 | 6/2001 | Gonzalgo et al. .............. 435/6 |

*Primary Examiner*—Gary Benzion
*Assistant Examiner*—Cynthia Wilder
(74) *Attorney, Agent, or Firm*—DLA Piper Rudnick Gray Cary US LLP

(57) ABSTRACT

The present invention provides a method for detecting a cellular proliferative disorder in a subject. The method includes contacting a nucleic acid-containing specimen from the subject with an agent that provides a determination of the methylation state of at least one gene or associated regulatory region of the gene and identifying aberrant methylation of regions of the gene or regulatory region, wherein aberrant methylation is identified as being different when compared to the same regions of the gene or associated regulatory region in a subject not having said cellular proliferative, thereby detecting a cellular proliferative disorder in the subject.

7 Claims, 14 Drawing Sheets

FIGURE 6a

PL3-17, CSX, MINT23 MICP1 (SEQ ID NO:1)
cccgggcgcccggccctggctcgcggaatgggcggccagatctcaggccctgcgtgcccgagctcagtcccagttccaaccgggg
gtgcccatggactctcggagggcactcctgggggacagctaagacaccaggctgcaggatcactcattgcacgctgcataatcgcc
gccacaaactctcccgtgcgcaagaacaaacgcgcgtgggacagaaaaagttcctaggtctccgcaggagtgaatgcaaaatccag
gggactcagggtcatgttgggagcccccttctcccccccgagagtcagggagctgttgaggtgggatcggtgagggtcgcgccacgcg
ggtcccttccctaccaggctcggataccatgcagcgtggacactcccgagttgctctgcggaatcccggg P18-13 cyclinG micp2 (SEQ ID NO:2)
Cccggggagggtggttaccgctgaggagctgcagtctctgtcaaggtgagtgggactgcgcgagagttgaccgccagtgcgggtg
gggagctgggttgggggcgcggggcgaggagtaggtctggcccgcgcccttttccacactaaactctaccgctgttgtgagcacaag
cccaggctagtccgaggctggaggggcggagcggatccggcctcctgaggtgcctttcgtgtctgccgacccagtcccagggacta
gcctggggaggaagaatggaaccctgcagttagaggttcctcacatgactagctctgaagacctcctgccttcctgtctttagttggtgt
gggagggaccttccatgtatccagggcttagcttgtgcccggg PL-3-12 MICP3 (298 bp, ECEL-1)(SEQ ID NO:3)
Cccggggagagctgatcccggacagggggttccgaggaggtaaaggaagctccctggtgaaggtgagctctgcgcaggcgctgtgc
gggcagcccaggcactccgtcagcgccctctcaatccttaggaggagtcctccctgggtggtgctccagggctgtgggctggaccat
gacggcccccagctgcgtagctccagctcctttccaaccggttggtgggcggttccgagtggggacacgggatcggaggggactcct
gccgggtgtaccgctaccctcactagtcccgggatgcg P13-9 309bp, micp4 gad1 AC007405 (SEQ ID NO:4)
Cccgggacagagagagattgcgggctaatctgggtagatcgaggaccccacagagaagggcccaccggccatcgcctccacaccctc
cctccgacctcactcctagccccgcgcgcgcagtcgcacagcaactcgggcagcgggtcgactacggcccctggaaaagtaacag
gttaccgttcctagtagcgccttcggctgctgctgcccaggcgcccttggagggacaggcgctcgcagcatggaagctcaagggaa
aatcgctcttgccccacttcaactagagcctcagcctccgtgcttccccggg PL3-18, 2$^{nd}$, ICAM-5 (630 bp, MICP5)(SEQ ID NO:5)

Cccgggagcatgcgggcacttaccgctgcgaagccaccaaccctcggggctctgcggccaaaaatgtggccgtcacggtggaatg
tgagtaggggcaccgcggagttaggcaggatctgtgggacaacccggctggacttcctggccccgtgtgagcccctgcaatcctg
tttcccagatggccccaggtttgaggagccgagctgccccagcaattggacatgggtggaaggatctgggcgcctgttttcctgtgagg
tcgatgggaagccacagccaagcgtgaagtgcgtgggctccgggggcaccactgagggggtgctgctgccgctggcaccccaga
ccctagtcccagagctcccagaatccctagagtcctggcacccggtatctacgtctgcaacgccaccaaccgccacggctccgtggc
caaaacagtcgtcgtgagcgcggagtgtgagcgaggcccaggcgggtagggagcagggtgccccacggtccaggcactccctga
catcccccatggctgttttgcagcgccaccggagatggatgaatctacctgcccaagtcaccagacgtggctggaagggctgaggct
tccgcgctggcctgcgccgcccggg P18-9 308bp, micp6 AF132611 MCT3 (SEQ ID NO:6)
Cccgggtggtgaccctgccctgcccacaggccccgtgtccagcatcctcgtgacccgctttggctgtcgcccggtgatgctggcggg
tgggctgctggcttccgcgggcatgatcctagcttcctttgccacgcgccttctggagctctacctgaccgctggggtgctcacaggtga
gggcccctggtctcctctccgctgggttgggggtcggggggttcttgctgcaagatctgtcctcggtttccctatgagggacagtcttcg
aagtccctcggctgggttcccggatctgctgggttcccggg

FIGURE 6b

P18-17 548bp, micp7 pax5 (SEQ ID NO:7)
Cccgggaatccacagccacatttccgattgtggcgaaatctgctcagtggctctgcgatgtccagttgccgccggggggccccccttcc
tcgagctctaggctcttcccctaggttgcgacccagcctcgtgaccacccctccaaaaaaacaaacaacactcttgctgaggacgat
tcactctccaaaactgcattgtccggcgggccaggagtctctacggacgcgtcccgcctgagacttccctcgagccaccgctgcagg
cccacggcttcagtggctaggcccagcagctgaaccaactcaaggctggggggaacaggagggaggcttgagtctggcccgaag
agagagggctggacatgccacacctctgctcggtctctgtggatctgatttcctctctggaatcaagtcctggggctctgggactccaca
acgtctcagggctcgagggcaatgcgattccacttacgggccggggtaaggtgtctggaactcccgccaatctccagaaactactgag
atgttctgctctgcccggg P13-50 255bp, micp8 ppENK (SEQ ID NO:8)
Cccgggaaccgcgaggcgatctgagtcgcctccacgtctacctaaaagctgtcggccgggagggcggggccccagaaaggagca
ttcctgcgggcttttgctcgacgatcccctgctgaggctgtcgcggcgagggtcctgccgagggaccccgttctgcgcccaggcagg
ctcgaagcacgcgtccctctctcctcgcagtccatggcgcggttcctgacactttgcacttggctgctgttgctcggccccggg P13-3 431 bp, MICP9 (SEQ ID NO:9)
Cccgggcagagctcggagcgcctccatccccggaaccaggggactccctggagtgctccggtccaggctacgatcgaggcgccc
ccatcccttgggccagggagaggatcggagacaccaggaggccctcggggctgggtgaagatctttggttccgggggtccggga
gaggatccacccctcccaatacccccgactcccagggctctgaccaagaatggaggtgcccccttctccaggcctcgagccctctgagcg
ccgaggccggccgcctacaggtcccccgccgctgggcggaccctctcattcggttccctcacgtcaccgctgtccggcgcctggga
actgggctcctggaatttcctctcctggggctgacagatggccctcttttccttctctgcggcagcctcgcccatcccggtcccggg PL3-14 MICP10 (600bp) (SEQ ID NO:10)
Ccggggacggggagggaggagggctgccgggatgtgaaccggggaaggcagctgggggctggagagcagcgcggaaaggg
ggcccagggagctggaaagagggccaagaggagggcaaggaaggtggcgggcgacggggagaggaaagaaaaagggtgtctt
ggcggtggccttggtaagagaaaggggcaaggggtataattgacaaggcactgaaagtattgaagtcagagccttgggaaggatcta
ccgaactctcggcggtccacgcggggacagacctcagcccgtgagccttgagctccacgcggggacagacctcagcccgtgagcc
ttgagctccacgcggggacagacctcagcccgtgagccttgagctccacgcggggacagacctcagcccgtgagccttgagctcca
cgcggggacagacctcagcccgtgagccttgagctccacgcggggacagacctcagcccgtgagccttgagcccagaaggagtgg
cagcctcaggacgtttgccaggtggcctggaatgtgagggaagcctcagccccgccaggaacagagctggcgctgagttcccggct
cggcccggg PL3-23 359 bp, MICP11(SEQ ID NO:11)

Ccgggggcgcacgggcgtgagggtggggtctcatcgcaggggcgccgggagcctccccgctccgctagctcaaccaaggaccg
ctcagaggggctctcaccctgaacctcggcttttctaaaggagcgagaccagattcccttctcttctcgacgtcgtttggtgttttctcgttct
tttcgactgagcacggcaatgcgcagacgtcgacgtctctcactgctcatcccgatctgtaacctgaggtgagcccgaagaccgctgc
cgccggcggccacccccagcgcgggtccgctgaggatggaaacagcaagtgcgcgccggccaggccgccacctctccctcctcca
acagcccggg

FIGURE 6c

PL3-25 370bp, MICP12(SEQ ID NO:12)

Cccgggaggtagcgggagattgcacacgcgatcctgcgagtttccgaactttggaagatcgtgacccggagagacccttgggagga
gagggccggccacctcctaggggtgctgtttttttaagggtcaacccaggacgctacgggaagcacctggcgcatccttggaacagtg
ggcttggtggcccaccgcaacgcctggcgggaaggaatggcggggcatcgtgtgcctaatggaccccgtcacagaccogccccaa
tccgagggggcggatgagctcagaggacctgcccaggacgctccttctccactttccaggaaaaccgacggcgtgcgcgcctccgtgt
cctcgcggagctggggtccccggg PL3-32 324bp, MICP13(SEQ ID NO:13)

Cccgggcctgggctgtgccagcccggcctgccagtctcggcccccattctcgtacggagggatgcggcgcctggggcctcgaagc
tccgggcggttttggagaagttgaagctcagccgcgatgatatctccacggcggcggggatggtgaaaggggttgtggaccacctgc
tgctcagactgaagtgcgactccgcgttcagaggcgtcgggctgctgaacaccgggagctactacgagcacgtgaaggtgagctgct
tggcgccctcccgccgagccccgctgctcggccttccgcaatccgcagtccctaccttccccggg P13-49 392bp micp14(SEQ ID NO:14)

Cccgggaaagacctcgagagaccttcttcaacacgtctccaggccagattcccctaccatggctcgggagcaatgacgcgctccccc
tcgccactcgcatggagacccgacttccctggcgccccacgagaggctcactgacctcgccgtcgtacctcgtgagagaccgcacct
gggccgcgtcgagacacccgagattccccgtcaccgagagcttgaggccttcgtctcctgcatggcctagagaccaatctcgcgacct
gtctccaaacgccctcaggaggcttgactcccttgagtccgcccagtgagctccaagagatacccgtcgcgattcgagagcagagcg
gggttctttgcttccactcgagatgaatgcctgtctccccggg P18-1 358bp, micp15 AP000913.2(SEQ ID NO:15)

Cccgggagaggcgacagcctcatccgtttatttcctcccttgaccatttgttcagcgactctcccctccgttcagcatccaggttccttacg
gctacagtgccccagccccgcctcaccagcgcgacattctgccctgcctacccactcagacacagtgccctttcggttcttcaaacttg
ctaagcgttttcctatcgatatctgcaggtaacagatggcacgctctcaaatagggtaatcggaggagggtctaataaaggaactatttc
aacagcggagtaggcgttagggactccagtaggagtagggctgtgtcccaggatactaacagcagggcgccttggccgccccggg P18-5 545bp, micp16(SEQ ID NO:16)

Cccgggctgtgcggagatgcgcaggcttggggcggcgttcaggagggactgggaaagggatcgtgccctagggtctcctggtgcg
aaagggtgcggcgcagcaggtgggatcaggtgaggtccgctggcatttatggggtgggtggtggaaaattggaaagagtttccgg
ggagttgtggaagactccggaaagaagggtctgttgaaggcggtgtgttgaaaggatgtaggggaatgacagaggggtgttttaggg
gtccaattgggtgaggtctggggggaagatatcgagagggtcatgggcccaggagtgcacgtctaggagttgatggggtaggcct
gagggttcggagaaggtgcggtcggggaggagtctcgcgattgagtttgtcggggcgggcgggaagctgacagctgcctctgtggt
ctcaggaggcggactccgccggtgcagccgcccccgacgcgggaggaccgggcctcatcgtcccgggagcgctccgcgtcgcga
ggccgcggcgccgcgcgctcctcatcccggg

FIGURE 6d

PL3-16 MICP 17(510 bp, MINT 20) (SEQ ID NO:17)

Cccggggggcgctgaggttgccttctcaggcggaggaggcgaaccctgtagcccgacaacgccgggcttcgattttgaggagcttc
ttccgggatgtcgctatactggccggagacgggccttgcgtgtccattgggggatggcgatggggaccagtttccgggtagagaagg
agataactcgatacaggaacgcacaggcagcctgaaagcagcccaggatctcgacaggggaagggaagaccctgctcccttgccc
aaatcctcccgccctgtccttgccttctgtcccagatcccaagcccctcgtacctgcactcgggactcggtcagcccgatacgcagtgc
cagctcctcacgcataaagatgtcggggtagtgagtcttggcgaagctcctctccaactcgttgagctgtgcggggggtgaagcgcgtc
cggtggcgcttctgcttctgttggccctgctgctggccggcttggctggggttcgggccgccctggggcccggg P13-8 386bp, micp18 AC005998(SEQ ID NO:18)

cccgggaaacagttcaggacgctcaagaccagaagcgggagcaaacccaaaaggagctccaaggaggtgtgtgtggggagagcc
aggggacgcaggactaggctctttcctgcgcaaggggtggggaaacccgcgaaagccagggagtcgcgcgcactcacgccctc
gcgccaccaggcagagccaccgctgcaaggagcccacgggtgcgcgctcgctccagggcggatctttccacaccccctcacccct
caaaagctcaggctggagcggtcatcagtgcggactccggcaccccacccacccagcaggggttaaggagggactggcgcccact
cttgcctacagctcctgcgcagggctccagccgccaaatcttcccggg PL3-33 514bp, micp19(SEQ ID NO:19)

Cccgggctgaatggtagacgttctggcgccgggcagcggccaccggctggttcccacttccgcgcgcacccccttaaactgtgttcta
gaggccccagcctcgccttgcagcgcctcactagctcctgaggactagggactcggcggtgaggcgggttggcggctcgaacgag
ctgggcgtcttcgttctctctcgctgcctggctggctcagctggccctccacagctcggagcaaggccatagcagggagtggaggtat
attgggctgtcacctccttgctggccggagttatttgtagactacagactcggaagaacagacgcgccacgctctcgcttggcattgcttc
ggatcgcagctcctccttgggtgccccagcttggcgtttatttgcctgcgccaggctctggcnacggtcaccgggccagcggggag
ggacggacggcaggtgaccagcctctgctgtgaagaaattcctgcgcgcccggagctgtccctaatgcatcccggg P13-51 279bp, micp20(SEQ ID NO:20)

Ccggggatcgggagcttggagtgaggngctcggcgtgacccgtgaggagccccgcgggtagagcggcgctgccccttcgctccg
gggtgaactgaaactttgctaggggagagggtcggcgccagcctcgcggggttcggagaagacccagcgctgtgcgaggtcgggg
ccgggcagggcagagcagggtgaaaggagagacctgtaatgacggcgggatttgggtgcggagggttgcgagggaggggcc
gcaaccctgaacaattgcattcccggg P18-21 422bp, micp21(SEQ ID NO:21)

Cccgggtctggcttggtctcgcccgcgcagatcccgttcaaactcagctgccaccaagtgcgccttttctctctggattgcgattctgca
cgaattttccagttgagggtggttcggcgctcagccagcctctgccctcgaagacgcggccttggtctaggaaccttcaggtgggtgttt
gggcgcagtggccctagttccctagaattcgttttgcctcccgcggcctcagccgcgtggtcagcgagctcgcgagaacgcagctgg
gcagtcccggacggctctcgggcgcttctagggagcagtcaaaggggttgcgaggactgccagggtccttcctccctaggcttcccac
actggatggccgtaactcagtcgttgacggcgacagccagggccctgatggactgtgcaggtcccggg

FIGURE 6e

P13-18-2 mint32, 464bp, micp22(SEQ ID NO:22)

Cccgggtacctgcacagctcgctccctcccatccttcgggtcttcgctcgaacgtccgctcctcggtgaggccttccctggacaacgca
tttgaaacgtaaccccaaggcaagaagccaccttccaggcgcgcagccgaagcccagtgccaaggaggccggagactcgggtgcc
cgcgcatcccgaaaacagcctctgagggtcctctgagcatccttccagcgtgtttgggaggcaaactcgttgactagctcttgagagg
agtggctagaggaatccaggcggggaaggggacggtggactccaggagagtgtaatttacaaaggcggggggcggggacgccca
ggtccgagtcccaggactctgcgccggacgcttcgcccgcccttcaggtcccctgcccggtcctcgtacccgcgcgggtccggaga
acctctgagcaccggccccagcccccggg P13-4 257bp, micp 23(SEQ ID NO:23)

Cccgggatcggtgcccgttagtgggcacaggacgccgggtgtccgaagggctgcctggagatgcaactgaccttggcgggcatca
gaatgacgagtggcagcagcaggagcggggtgacgaacaagatcacgaaggacttgaacttggagacatagctcagcgccgagg
ccatcgcgcgggagggagactggcgggcgagacgagtgaggggcagctagaggcgccgcgggcttaagaaggggccacagtc
cccggg P13-5 350bp, micp24(SEQ ID NO:24)

Cccggggatggcgcgccaggtaaggcaggcggacgcgcggacccctcggcgcagtgcggccccgaaggcggtagggcgaga
aagagctgggaccccccccgcaacttcgggatcggctgggtgaggctgggcaggcctgatgctcaggggttcgtgccgggaagttca
ggtcctcggacaacctctctccagctctccgccgccggtacccacggcccagtctccacctggggaaaccccttggcgtggcttgttt
cgttacaagttatcctggtagagtgggcatgaaggcctcggaggcagtgagtaaatctcatacttctgttcttggtggaatcctggatccc
ggg P13-6 337bp, micp25(SEQ ID NO:25)

Ccccgggctgccggctggagcccggcagattcgctgcgcagcactgcccctggtatccagcgccgaaagtgccccctccgcag
ctgcaaggctcctccctgggctgcgcgggacagattttctcctttcctggctacacgcctaacagagaagctatcccgagggacctca
agaagtccccccaagccgtactcaaaagcctttctccctcctcctcaagcgctcacttccccaaagaggacccggacccctgactgcct
gagccaggtccccagcatggtccgcaaccctttctcgactccggcatccacctccaggctgacgtctacccggg PL3-11 MICP26 (229 bp) (SEQ ID NO:26)

Cccgggggaaagagatgagtggaaatcgtgggccggacctgcaaggagagactcggcgggcaccttgcttggtctgaggtcgtct
gcaggaagcggactttctcctggctcaggatgggaaagacaggggatgcctgaagtcaacggggacttctgttccatctctgccccgt
tctccaggcccgccagttttcctgctttggttagattttccaacgtatcccggg

FIGURE 6f

PL3-13 MICP27 (427 bp) (SEQ ID NO:27)

Cccggggctgctgaccgagccccagggcagcccgcccttcccctcctgaagcccgacgtcttcttcatggctccgtctaccggcttc
ggagacccgctggacttttcgccgcctccggaaccctatatgaggaagcaaatcgcgtccgccacagcctccaactaggaaactccg
cgactctcagccccctcagaagagaaacggagacgcgccaagcaaagccgttacacggactgtgcacgcgcctccggtgtccctgcg
cgtgacacaaatttggccccgagggagctccatgtgcctgagtcccaggagccctagatgccagcgacagcttgtcaccaggcctgc
gacgccaatgggcgggagtcggcggagctcaggacactgacgacgggcctgggggaaagcggtccccacacagcccggg PL3-19 (470 bp, MICP28) (SEQ ID NO:28)

Cccggggacagggggaccccccagatgctgcacggctgacaggccaacgtggcagaagctccagcttcacaggaagccagtgacc
atgagagtctgtagctgtaacgaagccacagagctgtggctttctttcccccttcagctctaggaaaggttatctgccctgcacagatctcc
ggaggcctggctgggctctgagagcatcagactgattatcgtaagaaaataatctctgcagacacattccttgctagaagcaggggaca
aagcccagcttcaaagacaattccacacacgccctccctgccctgcacagctgcctgccgggtgggagcagagcccttgcagccgg
gctcaggggcctgggcagggacagcgtgtggcaggggcacagctgagacaggagcctcaaagcgacaccaacccgacgtgaag
ctacagttgaggagacacagctgcccccattcccggg Pl3-20 (bp 264, MICP29) (SEQ ID NO:29)

Cccgggcggcggccggattgcgggtgggtgagaggcagcagacgccgtgtttacagctctctcgctagttcgccacctcagccgcg
gctctagggctgagccagtcgcctccttctttaagattctggtcacagcaggggctgggtttctaaggcaggtttctaaggtgtcttcctac
agacaccgctgctgctaccttgctaccttcagcgctgggcacagccaggggcagcgcgagagggaggcaacgagagggttcccgg
g Pl3-21 (bp 371, micp30) (SEQ ID NO:30)

cccgggaccccaatgccagggaggggcctgcaggaccccagcggtgggcgagttgtgtcctgggtcaccttgtgtttcgcagcgtg
gcggtggcaggagcccagcgcggggaggacattttcatagcctcctacagtgagaaacgccccccacccgacgctgcgctcatctgtg
tccccgctgttgccggggctctggtatccacttgcgcgccctatgtggtggggatccacccagagcccagcgtcaagttatacgggcg
cttcactcagcgtcagccaagaccagggaagcgcttcttgccgtttaggagacgtctgcaagagataaaaagctagcccacgatccac
ccacaatcctcgtgtccccggg PL3-22 bp 179, MICP31(SEQ ID NO:31)

Cccgggaactcgcggcacccactgggtattgtcgggacccagcaagtctaggaacgggggtgggtagagcatccttcgggcactg
ccgttcgtccccaaaagaagaccaccgcggggtcccagggccacggcgaggacgggcactggtcagattccggacaggcggtcct
ggcccccggg

FIGURE 6g

PL3-34 445bp, micp32(SEQ ID NO:32)

Cccgggctgtgaccagcgaattcgggccccgcaggtgcagctgataggagaaatccggctccgggagcgaacccagcggcggaa
aggcgggctccgcgcccaggcgggccttggactgcaagaaggcgaggatgcgcgcgtacttcgtgtccttggtctcatcgtcacgtg
tgagtatcgaccaggtcatcatcgcacgtggtaccatagtggaagtagttggcaaactcgctagagtctgctggaggaacgagcccgc
cgtaggacggacacacctgagtgcccctcccacgcgagcccaaagcgggtgcagggcacctcccaccacatttctggccaaagttc
ccatttgaggcccgccctctcctctgcgcagtcttagagactggcgaggcacgcgcaaacgccctcttccctgagacctgaccccacc
cacccacccggg P18-2 357bp micp33 AC002133(SEQ ID NO:33)

Ccgggggagccccggaccccgcatcccccagggcgcggaaactggcgaggccccaggagctcccatttatagctcagtttccac
tgagcgcagtccctctaggacctgggctgagcaagtttcttccactctctcccttccctcctcctacccccttgcctgcccctcaacccccg
gcagggcgcaggtgtccaacccagccgggaccccctccctcctcgaacccaggtgttccggctcccagaccccaattgagctgggg
gcgcccaccgccgggggatcccgccctgcgtccccattcatccgcgtctcagccgcgggagtttctcaacgggaagagggcgga
gctcccggg P18-3 312bp, micp34 AC005826(SEQ ID NO:34)

Cccgggaggagagttggggcttgggggacgccgtgaactccatggtccccagcacgcggtcctggccagggacggggtcgtccg
aactgccgtccagattccccaagggagacaaagacccgaaacacagctcaaagtttccgagagcagtcacagcggggccagggac
tccagaagtgtcagctccaacgactccagagctgcacactggcctctattccccaccgcaaagccccagagccgcagagacttcgaa
ggcagccggagaggagagggcccaccgagcactacggcgggtgcgcacgccccggg P18-6 372bp, micp35(SEQ ID NO:35)

Cccgggagccggctcgctggcggcgccaggccacgctctctcattaacatcccgctcccggtggcgcaggggagccggccaaagt
tcctcgcaaagtggcgagcgaaggagcgctgagcactgacgtctgggctggggaggagcgggtccgagcgaggacggagaggg
gacagagggaaagggaggcgggtgtcttcctcaggaatttgagctggggatctgcatcctggccattgcagtcctttagcatcctcgcc
gcgccctgagcgcgctggaggctcgcaggctgcgccctcccagggctgatgccgcgtcctgctccgccgttctgggacgtcgggga
caaaagtggaggagacgggagagcccggg P18-7 399bp, micp36 AF132611(SEQ ID NO:36)

Cccgggctgcgagcgcggctcctggattccagcctcccgcccttccaggcgctggaatggacacggacgcccacagtggcgggc
caggtagtgccggagtcggggggcccaggccgcggcgccccgcgcctcatcacttaccttgcctttagctatcaattccatgatgtagcc
aaattcactcatctccccagactccgacatgtttacaccccttcacaaactctggaggaccgacgcgggtgtatcgaatttgtcctttcttt
ctcttttctgtttttagtctgagttttgccgagctccccgcccataagctgttaaccaggaaaagaggggaagcgccggggaaagcaag
aagcgggcttgggtgaaatgaaggccatcgagggctcccggg

FIGURE 6h

PL3-31 307 bp, MICP37(SEQ ID NO:37)

Cccgggcccggtgcgcaccggtgccgacttggcagccgccctgtgcgctcgacgaaagggtgagaaggaggcaggagtgcagg
cggaaggagtgggcaatcagcggcggggacgagagtgtgtcttcggggaaaccaagtctgagtgagcgctgaaggggagtgtgcg
gagcgtgccgtgcaccccgagcccccgcctcattgcctctcgcctctctccacctgccccatgatctgcgccagggaccggtcctct
cccgtccgcaggctgtctaggtggccgttctggtttgctgggacccccggg Pl3-37 331bp, micp38(SEQ ID NO:38)

Cccggggccacctctgaggcatgaacccagagacgcgcgccctggtctgggaaagcaggaccgctgcgcccagcgcctcaggg
gtagaggcgggaacaggcccgcggtcgctttgctggcggcggggaagggcgatctgacgatcagggagttgcgcccctctctctgg
gcctcgtgaaggaacaagagcaattacagcgctgggccggccacgtagtcctggggctaggtgggcccaatgctccgggccgcgg
ggctggagcgcggaggctggagagggaggaggacccctccgcggctccaggtctcccagctggaggctcacgcccggg Pl3-43 304bp, micp39(SEQ ID NO:39)

Ccgggcccggtgcgcaccggtgccgacttggcagccgccctgtgcgctcgacgaaagggtgagaaggaggcaggagtgcaggc
ggaaggagtgggcaatcagcggcgggacgagagtgtgtcttcggggaaaccaagtctgagtgagcgctgaagggagtgtgcgga
gccgtgccgtgcaccccgagcccccgcctcattgcctctcgcctctctccacctgccccatgatctgcgccagggagccggtcctct
cccgtccgcagctgtctaggtggccgttctggtttgctgggccccggg Pl3-44 307bp, micp40(SEQ ID NO:40)

Ccggggggtcccagcaaaccagaacggccacctagacagcctgcggacgggagaggaccggttccctggcgcagatcatggggc
aggtggagagaggcgagaggcaatgaggcgggggggctcggggtgcacggcacgctccgcacactcccctccagcgctcactca
gacttggtttccccgaagacacactctcgtccccgccgcgtgattgccactccttccgcctgcactccagcctccttctcacccttttcgtc
gagcgcacaggcggctgccaagtcggcaccggtgcgcaccggcccggg MICP41 also known as PL-3-2, 43(SEQ ID NO:41)

Ccgggcccggtgcgcaccggtgccgacttggcagccgccctgtgcgctcgacgaaagggtgagaaggaggcaggagtgcaggc
ggaaggagtgggcaatcagcggcgggacgagagtgtgtcttcggggaaaccaagtctgagtgagcgctgaagggagtgtgcgga
gccgtgccgtgcaccccgagcccccgcctcattgcctctcgcctctctccacctgccccatgatctgcgccagggagccggtcctct
cccgtccgcagctgtctaggtggccgttctggtttgctgggccccggg FIGURE 6i P18-19 479bp, micp42 3' of FLJ00083(SEQ ID NO:42)

Cccgggttcctggcttgaaccctgtttctccctgttctgccaggcatgctggtccggaaggtgtgtgtngctgtnggctttaggtgggtg
cagcccgtcccacgtcacggcgagctctgtttcctgggctggggacagtgaggtcatcgctgcccatcctggagctctggctcctttcg
ggtacctgttccctctcccagagagaccccccagctgcatgcaggcctagtgggctccacggcggagctggttcccaggctacctgggt
tgccacctctgtgggtcccggctgccctctcgcagccgccgctacttcctcaccctcttggccctgcatttccacgtctcatggagccaa
cgagagcaggggggtttgagcccttgtggaaatctggggaggcactgcttctccctccatgtgagcagcttcacccagcctggggtcag
tgcttacgctccacgcggcctggccttccccggg

SEQUENCE LISTING

<160> NUMBER OF SEQ ID NOS: 114

<210> SEQ ID NO 1
<211> LENGTH: 414
<212> TYPE: DNA
<213> ORGANISM: Homo sapiens

<400> SEQUENCE: 1

```
cccgggcgcc cggccctggc tcgcggaatg ggcggccaga tctcaggccc tgcgtgcccg     60
agctcagtcc cagttccaac cgggggtgcc catggactct cggagggcac tcctgggggg    120
acagctaaga caccaggctg caggatcact cattgcacgc tgcataatcg ccgccacaaa    180
ctctcccgtg cgcaagaaca aacgcgcgtg ggacagaaaa agttcctagg tctccgcagg    240
agtgaatgca aaatccaggg gactcagggt catgttggga gcccttctc ccccgagag     300 tcagggagct gttgaggtgg gatcggtgag ggtcgcgcca cgcgggtccc ttccctacca    360
ggctcggata ccatgcagcg tggacactcc cgagttgctc tgcggaatcc cggg          414
```

<210> SEQ ID NO 2
<211> LENGTH: 392
<212> TYPE: DNA
<213> ORGANISM: Homo sapiens

<400> SEQUENCE: 2

```
cccggggagg gtggttaccg ctgaggagct gcagtctctg tcaaggtgag tgggactgcg     60
cgagagttga ccgccagtgc gggtggggag ctgggttggg ggcgcggggc gaggagtagg    120
tctggcccgc gccctttttcc acactaaact ctaccgctgt tgtgagcaca agcccaggct   180
agtccgaggc tggaggggcg gagcggatcc ggcctcctga ggtgcctttc gtgtctgccg    240
acccagtccc aggactagc ctggggagga agaatggaac ccctgcagtt agaggttcct     300
cacatgacta gctctgaaga cctcctgcct tcctgtcttt agttggtgtg ggagggacct    360
tccatgtatc cagggcttag cttgtgcccg gg                                  392
```

<210> SEQ ID NO 3
<211> LENGTH: 298
<212> TYPE: DNA
<213> ORGANISM: Homo sapiens

<400> SEQUENCE: 3

```
cccggggaga gctgatcccg gacaggggtt ccgaggaggt aaaggaagct ccctggtgaa     60
ggtgagctct gcgcaggcgc tgtgcgggca gcccaggcac tccgtcagcg ccctctcaat    120
ccttaggagg agtcctccct gggtggtgct ccagggctgt gggctggacc atgacggccc    180
ccagctgcgt agctccagct cctttccaac cggttggtgg cgcggttccga gtggggacac   240 gggatcggag gggactcctg ccgggtgtac ccgctaccct cactagtccc gggatgcg      298
```

<210> SEQ ID NO 4
<211> LENGTH: 309
<212> TYPE: DNA
<213> ORGANISM: Homo sapiens

<400> SEQUENCE: 4

```
cccgggacag agagattgcg ggctaatctg ggtagatcga ggaccccaca gagaagggcc     60
caccggccat cgcctccaca ccctccctcc gacctcactc ctagcccgc gcgcgcagtc     120 gcacagcaac tcgggcagcg ggtcgactac ggccctgga aaagtaacag gttaccgttc     180
ctagtagcgc cttcggctgc tgctgcccag gcgccctttg gagggacagg cgctcgcagc    240
atggaagctc aagggaaaat cgctcttgcc ccacttcaac tagagcctca gcctccgtgc    300
ttccccggg                                                            309
```

<210> SEQ ID NO 5
<211> LENGTH: 630
<212> TYPE: DNA

<213> ORGANISM: Homo sapiens

<400> SEQUENCE: 5

```
cccgggagca tgcgggcact taccgctgcg aagccaccaa ccctcggggc tctgcggcca      60
aaaatgtggc cgtcacggtg gaatgtgagt aggggcaccg cggagttagg caggatctgt     120
gggacaaccc cggctggact tcctggcccc cgtgtgagcc cctgcaatcc tgtttcccag     180
atggcccag gtttgaggag ccgagctgcc ccagcaattg acatgggtg gaaggatctg       240
ggcgcctgtt ttcctgtgag gtcgatggga agccacagcc aagcgtgaag tgcgtgggct     300
ccgggggcac cactgagggg gtgctgctgc cgctggcacc cccagaccct agtcccagag     360
ctcccagaat ccctagagtc ctggcacccg gtatctacgt ctgcaacgcc accaaccgcc     420
acggctccgt ggccaaaaca gtcgtcgtga gcgcggagtg tgagcgaggc ccaggcgggt     480
agggagcagg gtgccccacg gtccaggcac tccctgacat ccccatggc tgttttgcag      540
cgccaccgga gatggatgaa tctacctgcc caagtcacca gacgtggctg aaggggctg      600
aggcttccgc gctggcctgc gccgcccggg                                      630
```

<210> SEQ ID NO 6
<211> LENGTH: 308
<212> TYPE: DNA
<213> ORGANISM: Homo sapiens

<400> SEQUENCE: 6

```
cccgggtggt gaccctgccc tgcccacagg ccccgtgtcc agcatcctcg tgacccgctt      60
tggctgtcgc ccggtgatgc tggcgggtgg gctgctggct ccgcgggca tgatcctagc     120
ttcctttgcc acgcgccttc tggagctcta cctgaccgct ggggtgctca caggtgaggg     180
cccccctggtc tcctctccgc tgggttgggg gtcgggggtt cttgctgcaa gatctgtcct    240
cggtttccct atgagggaca gtcttcgaag tccctcggct gggttccggg atctgctggg    300
ttcccggg                                                              308
```

<210> SEQ ID NO 7
<211> LENGTH: 548
<212> TYPE: DNA
<213> ORGANISM: Homo sapiens

<400> SEQUENCE: 7

```
cccgggaatc cacagccaca tttccgattg tggcgaaatc tgctcagtgg ctctgcgatg      60
tccagttgcc gccgggggcc cccctttcct cgagctctag gctcttcccc ctaggttgcg     120
acccagcctc gtgaccaccc cctccaaaaa aacaaacaac actcttgctg aggacgattc     180
actctccaaa actgcattgt ccggcgggcc aggagtctct acggacgcgt cccgcctgag     240
acttccctcg agccacccgc tgcaggccca cggcttcagt ggctaggccc agcagctgaa     300
ccaactcaag gctgggggg aacaggaggg aggcttgagt ctggcccgaa gagagagggc     360
tggacatgcc acacctctgc tcggtctctg tggatctgat ttcctctctg gaatcaagtc     420
ctggggctct gggactccac aacgtctcag ggctcgaggg caatgcgatt ccacttacgg     480
gccggggtaa ggtgtctgga actcccgcca atctccagaa actactgaga tgttctgctc     540
tgcccggg                                                              548
```

<210> SEQ ID NO 8
<211> LENGTH: 255
<212> TYPE: DNA
<213> ORGANISM: Homo sapiens

<400> SEQUENCE: 8

```
cccgggaacc gcgaggcgat ctgagtcgcc tccacgtcta cctaaaagct gtcggccggg      60
agggcgggc cccagaaagg agcattcctg cgggcttttg ctcgacgatc ccctgctgag     120
gctgtcgcgg cgagggtcct gccgagggac cccgttctgc gcccaggcag gctcgaagca     180
cgcgtccctc tctcctcgca gtccatggcg cggttcctga cactttgcac ttggctgctg     240
ttgctcggcc ccggg                                                      255
```

<210> SEQ ID NO 9
<211> LENGTH: 431
<212> TYPE: DNA
<213> ORGANISM: Homo sapiens

<400> SEQUENCE: 9

```
cccgggcaga gctcggagcg cctccatccc cggaaccagg ggactccctg gagtgctccg      60
gtccaggcta cgatcgaggc gcccccatcc cttgggccca gggagaggat cggagacacc     120
aggaggccct cggggctggg tgaagatctt tggttccggg gtccgggag aggatccacc     180
ctcccaatac cccgactccc agggctctga ccaagaatgg aggtgcccct ctccaggcc      240
tcgagccctc tgagcgccga ggccggccgc tacaggtcc cccgccgctg gcggaccct      300
ctcattcggt tccctcacgt cacccgctgt ccggcgcctg gaactgggc tcctggaatt     360
tcctctcctg gggctgacag atggccctct tttcctttct ctgcggcagc ctcgcccatc     420
ccggtcccgg g                                                          431
```

<210> SEQ ID NO 10
<211> LENGTH: 600
<212> TYPE: DNA
<213> ORGANISM: Homo sapiens

<400> SEQUENCE: 10

```
cccggggacg gggagggagg agggctgccg ggatgtgaac cggggaaggc agctggggct      60
ggagagcagc gcgaaaggg ggcccaggga gctggaaaga gggccaagag gagggcaagg     120
aaggtggcgg gcgacgggga gaggaaagaa aaagggtgtc ttggcggtgg ccttggtaag     180
agaaaggggc aaggggtata attgacaagg cactgaaagt attgaagtca gagccttggg     240
aaggatctac cgaactctcg gcggtccacg cggggacaga cctcagcccg tgagccttga     300
gctccacgcg gggacagacc tcagcccgtg agccttgagc tccacgcggg gacagacctc     360
agcccgtgag ccttgagctc cacgcgggga cagacctcag cccgtgagcc ttgagctcca     420
cgcggggaca gacctcagcc cgtgagcctt gagctccacg cggggacaga cctcagcccg     480
tgagccttga gcccagaagg agtggcagcc tcaggacgtt tgccaggtgg cctggaatgt     540
gagggaagcc tcagccccgc caggaacaga gctggcgctg agttcccggc tcggcccggg     600
```

<210> SEQ ID NO 11
<211> LENGTH: 359
<212> TYPE: DNA
<213> ORGANISM: Homo sapiens

<400> SEQUENCE: 11

```
cccggggcgc acgggcgtga gggtgggtc tcatcgcagg ggcgccggga gcctccccgc      60
tccgctagct caaccaagga ccgctcagag gggctctcac cctgaacctc ggcttttcta     120
aaggagcgag accagattcc cttctcttct cgacgtcgtt tggtgttttc tcgttctttt     180
```

-continued

| cgactgagca cggcaatgcg cagacgtcga cgtctctcac tgctcatccc gatctgtaac | 240 |
| --- | --- |
| ctgaggtgag cccgaagacc gctgccgccg gcggccaccc cagcgcgggt ccgctgagga | 300 |
| tggaaacagc aagtgcgcgc cggccaggcc gccacctctc cctcctccaa cagcccggg | 359 |

<210> SEQ ID NO 12
<211> LENGTH: 370
<212> TYPE: DNA
<213> ORGANISM: Homo sapiens

<400> SEQUENCE: 12

| cccgggaggt agcgggagat tgcacacgcg atcctgcgag tttccgaact ttggaagatc | 60 |
| --- | --- |
| gtgacccgga gagacccttg ggaggagagg gccggccacc tcctaggggt gctgtttttt | 120 |
| taagggtcaa cccaggacgc tacgggaagc acctggcgca tccttggaac agtgggcttg | 180 |
| gtggcccacc gcaacgcctg gcgggaagga atggcggggc atcgtgtgcc taatggaccc | 240 |
| cgtcacagac ccgccccaat ccgaggggcg gatgagctca gaggacctgc ccaggacgct | 300 |
| ccttctccac tttccaggaa aaccgacggc gtgcgcgcct ccgtgtcctc gcggagctgg | 360 |
| ggtccccggg | 370 |

<210> SEQ ID NO 13
<211> LENGTH: 324
<212> TYPE: DNA
<213> ORGANISM: Homo sapiens

<400> SEQUENCE: 13

| cccgggcctg ggctgtgcca gcccggcctg ccagtctcgg cccccattct cgtacggagg | 60 |
| --- | --- |
| gatgcggcgc ctggggcctc gaagctccgg gcggttttgg agaagttgaa gctcagccgc | 120 |
| gatgatatct ccacggcggc ggggatggtg aaaggggttg tggaccacct gctgctcaga | 180 |
| ctgaagtgcg actccgcgtt cagaggcgtc gggctgctga acaccgggag ctactacgag | 240 |
| cacgtgaagg tgagctgctt ggcgccctcc cgccgagccc cgctgctcgg ccttccgcaa | 300 |
| tccgcagtcc ctaccttccc cggg | 324 |

<210> SEQ ID NO 14
<211> LENGTH: 392
<212> TYPE: DNA
<213> ORGANISM: Homo sapiens

<400> SEQUENCE: 14

| cccgggaaag accttcgagag accttcttca acacgtctcc aggccagatt ccctaccat | 60 |
| --- | --- |
| ggctcgggag caatgacgcg ctccccctcg ccactcgcat ggagacccga cttccctggc | 120 |
| gccccacgag aggctcactg acctcgccgt cgtacctcgt gagagaccgc acctgggccg | 180 |
| cgtcgagaca cccgagattc cccgtcaccg agagcttgag gccttcgtct cctgcatggc | 240 |
| ctagagacca atctcgcgac ctgtctccaa acgccctcag gaggcttgac tcccttgagt | 300 |
| ccgcccagtg agctccaaga gatacccgtc gcgattcgag agcagagcgg ggttctttgc | 360 |
| ttccactcga gatgaatgcc tgtctccccg gg | 392 |

<210> SEQ ID NO 15
<211> LENGTH: 358
<212> TYPE: DNA
<213> ORGANISM: Homo sapiens

<400> SEQUENCE: 15

| cccgggagag gcgacagcct catccgttta tttcctccct tgaccatttg ttcagcgact | 60 |

-continued

```
ctcccctccg ttcagcatcc aggttcctta cggctacagt gccccagccc cgcctcacca      120
gcgcgacatt ctgccctgcc tacccactca gacacagtgc ccttttcggt tcttcaaact      180
tgctaagcgt tttcctatcg atatctgcag gtaacagatg gcacgctctc aaatagggta     240
atcggaggag ggtctaataa aggaactatt ttcaacagcg gagtaggcgt tagggactcc      300
agtaggagta gggctgtgtc ccaggatact aacagcaggg cgccttggcc gccccggg       358
```

<210> SEQ ID NO 16
<211> LENGTH: 545
<212> TYPE: DNA
<213> ORGANISM: Homo sapiens

<400> SEQUENCE: 16

```
cccgggctgt gcggagatgc gcaggcttgg ggcggcgttc aggagggact gggaaaggga      60
tcgtgcccta gggtctcctg gtgcgaaagg gtgcggcgca gcaggtggga tcagggtgag     120
gtccgctggc atttatgggg tgggtggtgg aaaattggaa agagtttccg gggagttgtg    180
gaagactccg gaaagaaggg tctgttgaag gcggtgtgtt gaaaggatgt agggggaatga     240 cagagggtg tttagggt ccaattgggt gaggtctggg ggggaagata tcgagagggt       300
catgggccca ggagtgcacg tctaggagtt gatggggtag gcctgagggt tcggagaagg     360
tgcggtcggg gaggagtctc gcgattgagt ttgtcgggc gggcgggaag ctgacagctg     420
cctctgtggt ctcaggaggc ggactccgcc ggtgcagccg cccccgacgc gggaggaccg      480
ggcctcatcg tcccgggagc gctccgcgtc gcgaggccgc ggcgccgcgc gctcctcatc     540
ccggg                                                                 545
```

<210> SEQ ID NO 17
<211> LENGTH: 510
<212> TYPE: DNA
<213> ORGANISM: Homo sapiens

<400> SEQUENCE: 17

```
cccggggggc gctgaggttg ccttctcagg cggaggaggc gaaccctgta gcccgacaac      60
gccgggcttc gattttgagg agcttcttcc gggatgtcgc tatactggcc ggagacgggc     120
cttgcgtgtc cattggggga tggcgatggg gaccagtttc cgggtagaga aggagataac     180
tcgatacagg aacgcacagg cagcctgaaa gcagcccagg atctcgacag gggaagggaa    240
gaccctgctc cctttgccca aatcctcccg ccctgtcctt gccttctgtc ccagatccca     300
agcccctcgt acctgcactc gggactcggt cagcccgata cgcagtgcca gctcctcacg      360
cataaagatg tcgggtagt gagtcttggc gaagctcctc tccaactcgt tgagctgtgc      420
gggggtgaag cgcgtccggt ggcgcttctg cttctgttgg ccctgctgct ggccggcttg     480
gctggggttc gggccgccct ggggcccggg                                      510
```

<210> SEQ ID NO 18
<211> LENGTH: 386
<212> TYPE: DNA
<213> ORGANISM: Homo sapiens

<400> SEQUENCE: 18

```
cccgggaaac agttcaggac gctcaagacc agaagcggga gcaaacccaa aaggagctcc      60
aaggaggtgt gtgtggggag agccaggggg acgcaggact aggctctttc ctgcgcaagg     120 ggtgggaaa cccgcgaaag ccagggagtc gcgcgcactc acgccctcgc gccaccaggc      180
```

| agagccaccg ctgcaaggag cccacgggtg cgcgctcgct ccagggcgga tctttccaca | 240 |
| cccccctcac cctcaaaagc tcaggctgga gcggtcatca gtgcgactc cggcaccca | 300 |
| cccacccagc aggggttaag gagggactgg cgcccactct tgcctacagc tcctgcgcag | 360 |
| ggctccagcc gccaaatctt cccggg | 386 |

<210> SEQ ID NO 19
<211> LENGTH: 514
<212> TYPE: DNA
<213> ORGANISM: Homo sapiens
<220> FEATURE:
<221> NAME/KEY: misc_feature
<222> LOCATION: (415)..(415)
<223> OTHER INFORMATION: n is any nucleotide

<400> SEQUENCE: 19

| cccgggctga atggtagacg ttctggcgcc gggcagcggc caccggctgg ttcccacttc | 60 |
| cgcgcgcacc ccttaaactg tgttctagag gccccagcct cgccttgcag cgcctcacta | 120 |
| gctcctgagg actagggact cggcggtgag gcgggttggc ggctcgaacg agctgggcgt | 180 |
| cttcgttctc tctcgctgcc tggctggctc agctggccct ccacagctcg gagcaaggcc | 240 |
| atagcaggga gtggaggtat attgggctgt cacctccttg ctggccggag ttatttgtag | 300 |
| actacagact cggaagaaca gacgcgccac gctctcgctt ggcattgctt cggatcgcag | 360 |
| ctcctccttg gggtgcccca gcttggcgtt tatttgcctg cgccaggctc tggcnacggt | 420 |
| caccgggcca gcggggaggg acggacggca ggtgaccagc tctgctgtg aagaaattcc | 480 |
| tgcgcgcccg gagctgtccc taatgcatcc cggg | 514 |

<210> SEQ ID NO 20
<211> LENGTH: 279
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is any nucleotide

<400> SEQUENCE: 20

| ccggggatcg ggagcttgga gtgaggngct cggcgtgacc cgtgaggagc cccgcgggta | 60 |
| gagcggcgct gccccttcgc tccggggtga actgaaactt tgctagggga gagggtcggc | 120 |
| gccagcctcg cggggttcgg agaagaccca gcgctgtgcg aggtcggggc cgggcagggc | 180 |
| agagcagggg tgaaaggaga gacctgtaat gacggcggga tttgggggtgc ggagggttgc | 240 |
| gagggagggg ccgcaaccct gaacaattgc attcccggg | 279 |

<210> SEQ ID NO 21
<211> LENGTH: 422
<212> TYPE: DNA
<213> ORGANISM: Homo sapiens

<400> SEQUENCE: 21

| cccgggtctg gcttggtctc gcccgcgcag atcccgttca aactcagctg ccaccaagtg | 60 |
| cgccttttct ctctggattg cgattctgca cgaatttttcc agttgagggt ggttcggcgc | 120 |
| tcagccagcc tctgccctcg aagacgcggc cttggtctag gaaccttcag gtgggtgttt | 180 |
| gggcgcagtg gccctagttc cctagaattc gttttgcctc ccgcggcctc agccgcgtgg | 240 |
| tcagcgagct cgcgagaacg cagctgggca gtccggacg gctctcgggc gcttctaggg | 300 |
| agcagtcaaa gggttgcgag gactgccagg gtccttcctc cctaggcttc ccacactgga | 360 |

| | |
|---|---|
| tggccgtaac tcagtcgttg acggcgacag ccagggccct gatggactgt gcaggtcccg | 420 |
| gg | 422 |

<210> SEQ ID NO 22
<211> LENGTH: 464
<212> TYPE: DNA
<213> ORGANISM: Homo sapiens

<400> SEQUENCE: 22

| | |
|---|---|
| cccgggtacc tgcacagctc gctccctccc atccttcggg tcttcgctcg aacgtccgct | 60 |
| cctcggtgag gccttccctg gacaacgcat ttgaaacgta accccaaggc aagaagccac | 120 |
| cttccaggcg cgcagccgaa gcccagtgcc aaggaggccg gagactcggg tgcccgcgca | 180 |
| tcccgaaaac agcctctgag gggtcctctg agcatccttc cagcgtgttt gggaggcaaa | 240 |
| ctcgttgact agctcttgag aggagtggct agaggaatcc aggcggggaa ggggacggtg | 300 |
| gactccagga gagtgtaatt tacaaaggcg ggggcgggg acgcccaggt ccgagtccca | 360 |
| ggactctgcg ccggacgctt cgcccgccct ttcaggtccc ctgcccggtc ctcgtacccg | 420 |
| cgcgggtccg gagaacctct gagcaccggc ccccagcccc cggg | 464 |

<210> SEQ ID NO 23
<211> LENGTH: 257
<212> TYPE: DNA
<213> ORGANISM: Homo sapiens

<400> SEQUENCE: 23

| | |
|---|---|
| cccgggatcg gtgcccgtta gtgggcacag gacgccgggt gtccgaaggg ctgcctggag | 60 |
| atgcaactga ccttggcggg catcagaatg acgagtggca gcagcaggag cggggtgacg | 120 |
| aacaagatca cgaaggactt gaacttggag acatagctca gcgccgaggc catcgcgcgg | 180 |
| gagggagact ggcgggcgag acgagtgagg ggcagctaga ggcgccgcgg gcttaagaag | 240 |
| gggccacagt ccccggg | 257 |

<210> SEQ ID NO 24
<211> LENGTH: 350
<212> TYPE: DNA
<213> ORGANISM: Homo sapiens

<400> SEQUENCE: 24

| | |
|---|---|
| cccggggatg gcgcgccagg taaggcaggc ggacgcgcgg acccctcggc gcagtgcggc | 60 |
| cccgaaggcg gtagggcgag aaagagctgg gaccccccg caacttcggg atcggctggg | 120 |
| tgaggctggg caggcctgat gctcaggggt tcgtgccggg aagttcaggt cctcggacaa | 180 |
| cctctctcca gctctccgcc gccggtaccc acggcccagt ctccacctgg ggaaaccccc | 240 |
| ttggcgtggc ttgtttcgtt acaagttatc ctggtagagt gggcatgaag gcctcggagg | 300 |
| cagtgagtaa atctcatact tctgttcttg gtggaatcct ggatcccggg | 350 |

<210> SEQ ID NO 25
<211> LENGTH: 337
<212> TYPE: DNA
<213> ORGANISM: Homo sapiens

<400> SEQUENCE: 25

| | |
|---|---|
| cccccgggctg ccggctggag cccggcagat tcgctgcgca gcactgcccc ctggtatcca | 60 |
| gcgccgaaag tgcccccctc cgcagctgca aggctcctcc ctgggctgcg cgggacagat | 120 |

| | |
|---|---|
| tttttctcct ttcctggcta cacgcctaac agagaagcta tcccgaggga cctcaagaag | 180 |
| tcccccaag ccgtactcaa aagcctttct ccctcctcct caagcgctca cttccccaaa | 240 |
| gaggacccgg acccctgact gcctgagcca ggtccccagc atggtccgca accccttctcg | 300 |
| actccggcat ccacctccag gctgacgtct acccggg | 337 |

<210> SEQ ID NO 26
<211> LENGTH: 229
<212> TYPE: DNA
<213> ORGANISM: Homo sapiens

<400> SEQUENCE: 26

| | |
|---|---|
| cccggggaa agagatgagt ggaaatcgtg ggccggacct gcaaggagag actcggcggg | 60 |
| caccttgctt ggtctgaggt cgtctgcagg aagcggactt ttctcctggc tcaggatggg | 120 |
| aaagacaggg gatgcctgaa gtcaacgggg acttctgttc catctctgcc ccgttctcca | 180 |
| ggcccgccag ttttcctgc tttggttaga ttttccaacg tatcccggg | 229 |

<210> SEQ ID NO 27
<211> LENGTH: 427
<212> TYPE: DNA
<213> ORGANISM: Homo sapiens

<400> SEQUENCE: 27

| | |
|---|---|
| cccggggctg ctgaccgagc cccagggcag cccgcccttc cccctcctga agcccgacgt | 60 |
| cttcttcatg gctccgtcta ccggcttcgg agacccgctg acttttcgc cgcctccgga | 120 |
| accctatatg aggaagcaaa tcgcgtccgc cacagcctcc aactaggaaa ctccgcgact | 180 |
| ctcagcccct cagaagagaa acggagacgc gccaagcaaa gccgttacac ggactgtgca | 240 |
| cgcgcctccg gtgtccctgc gcgtgacaca aatttggccc cgagggagct ccatgtgcct | 300 |
| gagtcccagg agccctagat gccagcgaca gcttgtcacc aggcctgcga cgccaatggg | 360 |
| cgggagtcgg cggagctcag gacactgacg acgggcctgg gggaaagcgg tccccacaca | 420 |
| gcccggg | 427 |

<210> SEQ ID NO 28
<211> LENGTH: 470
<212> TYPE: DNA
<213> ORGANISM: Homo sapiens

<400> SEQUENCE: 28

| | |
|---|---|
| cccggggaca gggggacccc cagatgctgc acggctgaca ggccaacgtg gcagaagctc | 60 |
| cagcttcaca ggaagccagt gaccatgaga gtctgtagct gtaacgaagc cacagagctg | 120 |
| tggctttctt tcccccttcag ctctaggaaa ggttatctgc cctgcacaga tctccggagg | 180 |
| cctggctggg ctctgagagc atcagactga ttatcgtaag aaaataatct ctgcagacac | 240 |
| attccttgct agaagcaggg gacaaagccc agcttcaaag acaattccac acacgccctc | 300 |
| cctgccctgc acagctgcct gccgggtggg agcagagccc ttgcagccgg gtcaggggc | 360 |
| ctgggcaggg acagcgtgtg gcaggggcac agctgagaca ggagcctcaa agcgacacca | 420 |
| acccgacgtg aagctacagt tgaggagaca cagctgcccc cattcccggg | 470 |

<210> SEQ ID NO 29
<211> LENGTH: 264
<212> TYPE: DNA
<213> ORGANISM: Homo sapiens

<400> SEQUENCE: 29

```
cccgggcggc ggccggattg cgggtgggtg agaggcagca gacgccgtgt ttacagctct      60
ctcgctagtt cgccacctca gccgcggctc tagggctgag ccagtcgcct ccttctttaa     120
gattctggtc acagcagggg ctgggtttct aaggcaggtt tctaaggtgt cttcctacag     180
acaccgctgc tgctaccttg ctaccttcag cgctgggcac agccaggggc agcgcgagag     240
ggaggcaacg agagggttcc cggg                                            264

<210> SEQ ID NO 30
<211> LENGTH: 371
<212> TYPE: DNA
<213> ORGANISM: Homo sapiens

<400> SEQUENCE: 30
cccgggaccc caatgccagg gaggggcctg caggacccca gcggtgggcg agttgtgtcc      60
tgggtcacct tgtgtttcgc agcgtggcgg tggcaggagc ccagcgcggg aggacatttt     120
catagcctcc tacagtgaga acgcccccca cccgacgct gcgctcatct gtgtccccgc      180
tgttgccggg gctctggtat ccacttgcgc gccctatgtg gtgggatcc acccagagcc      240 cagcgtcaag ttatacgggc gcttcactca gcgtcagcca agaccaggga agcgcttctt     300
gccgtttagg agacgtctgc aagagataaa aagctagccc acgatccacc cacaatcctc     360
gtgtccccgg g                                                          371

<210> SEQ ID NO 31
<211> LENGTH: 179
<212> TYPE: DNA
<213> ORGANISM: Homo sapiens

<400> SEQUENCE: 31
cccgggaact cgcggcaccc actgggtatt gtcgggaccc agcaagtcta ggaacggggg      60
tgggtagagc atccttcggg cactgccgtt cgtccccaaa agaagaccac cgcgggtcc     120 cagggccacg gcgaggacgg gcactggtca gattccggac aggcggtcct ggccccggg     179

<210> SEQ ID NO 32
<211> LENGTH: 445
<212> TYPE: DNA
<213> ORGANISM: Homo sapiens

<400> SEQUENCE: 32
cccgggctgt gaccagcgaa ttcgggcccc gcaggtgcag ctgataggag aaatccggct      60
ccgggagcga acccagcggc ggaaaggcgg gctccgcgcc caggcgggcc ttggactgca     120
agaaggcgag gatgcgcgcg tacttcgtgt ccttggtctc atcgtcacgt gtgagtatcg     180
accaggtcat catcgcacgt ggtaccatag tggaagtagt tggcaaactc gctagagtct     240
gctggaggaa cgagcccgcc gtaggacgga cacacctgag tgcccctccc acgcgagccc     300
aaagcgggtg cagggcacct cccaccacat ttctggccaa agttcccatt tgaggcccgc     360
cctctcctct gcgcagtctt agagactggc gaggcacgcg caaacgccct cttccctgag     420
acctgacccc acccacccac ccggg                                           445

<210> SEQ ID NO 33
<211> LENGTH: 357
<212> TYPE: DNA
<213> ORGANISM: Homo sapiens

<400> SEQUENCE: 33
```

```
cccggggag ccccggaccc cgcatccccc agggcgcgga aactggcgag gccccaggag      60
ctcccattta tagctcagtt ccactgagc gcagtccctc taggacctgg gctgagcaag     120
tttcttccac tctctccctt ccctcctcct cacccttgc ctgcccctca acccggcag      180 ggcgcaggtg tccaacccag ccgggacccc ctccctcctc gaacccaggt gttccggctc    240
ccagacccca attgagctgg gggcgcccac ccgccggggg atcccgccct gcgtccccca    300
ttcatccgcg tctcagccgc gggagtttct caacgggaag agggcggagc tcccggg       357

<210> SEQ ID NO 34
<211> LENGTH: 312
<212> TYPE: DNA
<213> ORGANISM: Homo sapiens

<400> SEQUENCE: 34
cccgggagga gagttgggc ttgggggacg ccgtgaactc catggtcccc agcacgcggt      60
cctggccagg gacgggtcg tccgaactgc cgtccagatt ccccaaggga gacaaagacc     120
cgaaacacag ctcaaagttt ccgagagcag tcacagcggg gccagggact ccagaagtgt    180
cagctccaac gactccagag ctgcacactg gcctctattc ccaccgcaa gccccagag      240 ccgcagagac ttcgaaggca gccggagagg agagggccca ccgagcacta cggcgggtgc    300
gcacgccccg gg                                                        312

<210> SEQ ID NO 35
<211> LENGTH: 372
<212> TYPE: DNA
<213> ORGANISM: Homo sapiens

<400> SEQUENCE: 35
cccgggagcc ggctcgctgg cggcgccagg ccacgctctc tcattaacat cccgctcccg     60
gtggcgcagg ggagccggcc aaagttcctc gcaaagtggc gagcgaagga gcgctgagca    120
ctgacgtctg ggctggggag gagcgggtcc gagcgaggac ggagagggga cagagggaaa    180 ggaggcggg tgtcttcctc aggaatttga gctggggatc tgcatcctgg ccattgcagt     240
cctttagcat cctcgccgcg ccctgagcgc gctggaggct cgcaggctgc gccctcccag    300
ggctgatgcc gcgtcctgct ccgccgttct gggacgtcgg ggacaaaagt ggaggagacg    360
ggagagcccg gg                                                        372

<210> SEQ ID NO 36
<211> LENGTH: 399
<212> TYPE: DNA
<213> ORGANISM: Homo sapiens

<400> SEQUENCE: 36
cccgggctgc gagcgcggct cctggattcc agcctcccgc ccttcccagg cgctggaatg     60
gacacggacg cccacagtgg cgggccaggt agtgccggag tcgggggccc aggccgcggc    120
gccccgcgcc tcatcactta ccttgccttt agctatcaat tccatgatgt agccaaattc    180
actcatctcc ccagactccg acatgtttac accccttcac aaaactctgga ggaccgacgc    240 gggtgtatcg aatttgtcct ttctttctc ttttctgtt tttagtctga gttttgccga     300 gctcccgcc cataagctgt taaccaggaa aagaggggaa gcgccgggga aagcaagaag    360
cgggcttggg tgaaatgaag gccatcgagg gctcccggg                           399

<210> SEQ ID NO 37
<211> LENGTH: 307
```

<212> TYPE: DNA
<213> ORGANISM: Homo sapiens

<400> SEQUENCE: 37

```
cccgggcccg gtgcgcaccg gtgccgactt ggcagccgcc ctgtgcgctc gacgaaaggg      60
tgagaaggag gcaggagtgc aggcggaagg agtgggcaat cagcggcggg gacgagagtg     120
tgtcttcggg gaaaccaagt ctgagtgagc gctgaagggg agtgtgcgga gcgtgccgtg     180
caccccgagc ccccgcctc attgcctctc gcctctctcc acctgcccca tgatctgcgc     240
cagggaccgg tcctctcccg tccgcaggct gtctaggtgg ccgttctggt ttgctgggac     300
ccccggg                                                              307
```

<210> SEQ ID NO 38
<211> LENGTH: 331
<212> TYPE: DNA
<213> ORGANISM: Homo sapiens

<400> SEQUENCE: 38

```
cccggggcca cctctgaggc atgaacccag agacgcgcgc cctggtctgg gaaagcagga      60
ccgctgcgcc cagcgcctca ggggtagagg cgggaacagg cccgcggtcg ctttgctggc     120
ggcggggaag ggcgatctga cgatcaggga gttgcgcccc tctctctggg cctcgtgaag     180
gaacaagagc aattacagcg ctgggccggc cacgtagtcc tggggctagg tgggcccaat     240
gctccgggcc gcggggctgg agcgcggagg ctggagaggg aggaggaccc tccgcggctc     300
caggtctccc agctggaggc tcacgcccgg g                                    331
```

<210> SEQ ID NO 39
<211> LENGTH: 304
<212> TYPE: DNA
<213> ORGANISM: Homo sapiens

<400> SEQUENCE: 39

```
ccgggcccgg tgcgcaccgg tgccgacttg gcagccgccc tgtgcgctcg acgaaagggt      60
gagaaggagg caggagtgca ggcggaagga gtgggcaatc agcggcggga cgagagtgtg     120
tcttcgggga aaccaagtct gagtgagcgc tgaaggggag tgtgcggagc cgtgccgtgc     180
accccgagcc ccccgcctca ttgcctctcg cctctctcca cctgcccat gatctgcgcc     240
agggagccgg tcctctcccg tccgcagctg tctaggtggc cgttctggtt tgctgggccc     300
cggg                                                                 304
```

<210> SEQ ID NO 40
<211> LENGTH: 307
<212> TYPE: DNA
<213> ORGANISM: Homo sapiens

<400> SEQUENCE: 40

```
ccggggtcc cagcaaacca gaacggccac ctagacagcc tgcggacggg agaggaccgg      60
ttccctggcg cagatcatgg ggcaggtgga gagaggcgag aggcaatgag gcggggggc     120
tcgggtgca cggcacgctc cgcacactcc cctccagcgc tcactcagac ttggtttccc     180
cgaagacaca ctctcgtccc cgccgcgtga ttgcccactc cttccgcctg cactccagcc     240
tccttctcac cctttcgtcg agcgcacagg cggctgccaa gtcggcaccg gtgcgcaccg     300
gcccggg                                                              307
```

<210> SEQ ID NO 41

<211> LENGTH: 304
<212> TYPE: DNA
<213> ORGANISM: Homo sapiens

<400> SEQUENCE: 41

```
ccgggcccgg tgcgcaccgg tgccgacttg gcagccgccc tgtgcgctcg acgaaagggt      60
gagaaggagg caggagtgca ggcggaagga gtgggcaatc agcggcggga cgagagtgtg     120
tcttcgggga aaccaagtct gagtgagcgc tgaaggggag tgtgcggagc cgtgccgtgc     180
accccgagcc ccccgcctca ttgcctctcg cctctctcca cctgcccat gatctgcgcc      240
agggagccgg tcctctcccg tccgcagctg tctaggtggc cgttctggtt tgctgggccc     300
cggg                                                                  304
```

<210> SEQ ID NO 42
<211> LENGTH: 479
<212> TYPE: DNA
<213> ORGANISM: Homo sapiens
<220> FEATURE:
<221> NAME/KEY: misc_feature
<222> LOCATION: (1)..(479)
<223> OTHER INFORMATION: n is any nucleotide

<400> SEQUENCE: 42

```
cccgggttcc tggcttgaac cctgtttctc cctgttctgc caggcatgct ggtccggaag      60
gtgtgtgtng ctgtnggctt taggtgggtg cagcccgtcc cacgtcacgg cgagctctgt     120
ttcctgggct ggggacagtg aggtcatcgc tgcccatcct ggagctctgg ctcctttcgg     180
gtacctgttc cctctcccag agagaccccc agctgcatgc aggcctagtg ggctccacgg     240
cggagctggt tccaggcta cctggggttgc cacctctgtg gtcccggct gccctctcgc      300
agccgccgct acttcctcac cctcttggcc ctgcatttcc acgtctcatg gagccaacga     360
gagcagggg tttgagccct tgtggaaatc tggggaggca ctgcttctcc ctccatgtga      420
gcagcttcac ccagcctggg gtcagtgctt acgctccacg cggcctggcc ttccccggg     479
```

<210> SEQ ID NO 43
<211> LENGTH: 21
<212> TYPE: DNA
<213> ORGANISM: Artificial sequence
<220> FEATURE:
<223> OTHER INFORMATION: PCR primer

<400> SEQUENCE: 43

```
gagttggtga tgttagatta g                                               21
```

<210> SEQ ID NO 44
<211> LENGTH: 22
<212> TYPE: DNA
<213> ORGANISM: Artificial sequence
<220> FEATURE:
<223> OTHER INFORMATION: PCR primer

<400> SEQUENCE: 44

```
ttcccaaaaa aatcccaaat tc                                              22
```

<210> SEQ ID NO 45
<211> LENGTH: 22
<212> TYPE: DNA
<213> ORGANISM: Artificial sequence
<220> FEATURE:
<223> OTHER INFORMATION: PCR primer

<400> SEQUENCE: 45
ctccttccaa ataaatactt ac                                          22

<210> SEQ ID NO 46
<211> LENGTH: 19
<212> TYPE: DNA
<213> ORGANISM: Artificial sequence
<220> FEATURE:
<223> OTHER INFORMATION: PCR primer

<400> SEQUENCE: 46
agagaggagt ttagattgg                                              19

<210> SEQ ID NO 47
<211> LENGTH: 21
<212> TYPE: DNA
<213> ORGANISM: Artificial sequence
<220> FEATURE:
<223> OTHER INFORMATION: PCR primer

<400> SEQUENCE: 47
caaaaaaact aaaacctcaa c                                           21

<210> SEQ ID NO 48
<211> LENGTH: 24
<212> TYPE: DNA
<213> ORGANISM: Artificial sequence
<220> FEATURE:
<223> OTHER INFORMATION: PCR primer

<400> SEQUENCE: 48
tggataaagg atgtttgggg tttg                                        24

<210> SEQ ID NO 49
<211> LENGTH: 22
<212> TYPE: DNA
<213> ORGANISM: Artificial sequence
<220> FEATURE:
<223> OTHER INFORMATION: PCR primer

<400> SEQUENCE: 49
ccctcccctt acccctaaat cc                                          22

<210> SEQ ID NO 50
<211> LENGTH: 19
<212> TYPE: DNA
<213> ORGANISM: Artificial sequence
<220> FEATURE:
<223> OTHER INFORMATION: PCR primer

<400> SEQUENCE: 50 actcccccctc actttattc                                             19

<210> SEQ ID NO 51
<211> LENGTH: 24
<212> TYPE: DNA
<213> ORGANISM: Artificial sequence
<220> FEATURE:
<223> OTHER INFORMATION: PCR primer

<400> SEQUENCE: 51
attattttag tagaggtata taag                                        24

<210> SEQ ID NO 52
<211> LENGTH: 18
<212> TYPE: DNA

```
<213> ORGANISM: Artificial sequence
<220> FEATURE:
<223> OTHER INFORMATION: PCR primer

<400> SEQUENCE: 52
ccaaccccac ccttcaac                                                        18

<210> SEQ ID NO 53
<211> LENGTH: 20
<212> TYPE: DNA
<213> ORGANISM: Artificial sequence
<220> FEATURE:
<223> OTHER INFORMATION: PCR primer

<400> SEQUENCE: 53
aagagagggt tggagagtag                                                      20

<210> SEQ ID NO 54
<211> LENGTH: 24
<212> TYPE: DNA
<213> ORGANISM: Artificial sequence
<220> FEATURE:
<223> OTHER INFORMATION: PCR primer

<400> SEQUENCE: 54
cccctaaaaa aaaatcaaa aatc                                                  24

<210> SEQ ID NO 55
<211> LENGTH: 21
<212> TYPE: DNA
<213> ORGANISM: Artificial sequence
<220> FEATURE:
<223> OTHER INFORMATION: PCR primer

<400> SEQUENCE: 55
gggttggaga gtaggggagt t                                                    21

<210> SEQ ID NO 56
<211> LENGTH: 26
<212> TYPE: DNA
<213> ORGANISM: Artificial sequence
<220> FEATURE:
<223> OTHER INFORMATION: PCR primer

<400> SEQUENCE: 56
ygttatgatt tttttgttta gttaat                                               26

<210> SEQ ID NO 57
<211> LENGTH: 23
<212> TYPE: DNA
<213> ORGANISM: Artificial sequence
<220> FEATURE:
<223> OTHER INFORMATION: PCR primer

<400> SEQUENCE: 57
tacaccaact acccaactac ctc                                                  23

<210> SEQ ID NO 58
<211> LENGTH: 25
<212> TYPE: DNA
<213> ORGANISM: Artificial sequence
<220> FEATURE:
<223> OTHER INFORMATION: PCR primer

<400> SEQUENCE: 58
tttatttata taattttgtg tatgg                                                25
```

<210> SEQ ID NO 59
<211> LENGTH: 21
<212> TYPE: DNA
<213> ORGANISM: Artificial sequence
<220> FEATURE:
<223> OTHER INFORMATION: PCR primer

<400> SEQUENCE: 59
cacccctcac tttactaaaa c                                    21

<210> SEQ ID NO 60
<211> LENGTH: 23
<212> TYPE: DNA
<213> ORGANISM: Artificial sequence
<220> FEATURE:
<223> OTHER INFORMATION: PCR primer

<400> SEQUENCE: 60
tttgggaggt aaattygttg att                                  23

<210> SEQ ID NO 61
<211> LENGTH: 24
<212> TYPE: DNA
<213> ORGANISM: Artificial sequence
<220> FEATURE:
<223> OTHER INFORMATION: PCR primer

<400> SEQUENCE: 61
accraacaaa aaacctaaaa aaac                                 24

<210> SEQ ID NO 62
<211> LENGTH: 24
<212> TYPE: DNA
<213> ORGANISM: Artificial sequence
<220> FEATURE:
<223> OTHER INFORMATION: PCR primer

<400> SEQUENCE: 62
ttattagagg gtggggtgga ttgt                                 24

<210> SEQ ID NO 63
<211> LENGTH: 24
<212> TYPE: DNA
<213> ORGANISM: Artificial sequence
<220> FEATURE:
<223> OTHER INFORMATION: PCR primer

<400> SEQUENCE: 63
ttattagagg gtggggcgga tcgc                                 24

<210> SEQ ID NO 64
<211> LENGTH: 21
<212> TYPE: DNA
<213> ORGANISM: Artificial sequence
<220> FEATURE:
<223> OTHER INFORMATION: PCR primer

<400> SEQUENCE: 64
aggattggga tgttgagaat g                                    21

<210> SEQ ID NO 65
<211> LENGTH: 19
<212> TYPE: DNA
<213> ORGANISM: Artificial sequence
<220> FEATURE:

```
<223> OTHER INFORMATION: PCR primer

<400> SEQUENCE: 65
ggattgggat gtcgagaac                                              19

<210> SEQ ID NO 66
<211> LENGTH: 26
<212> TYPE: DNA
<213> ORGANISM: Artificial sequence
<220> FEATURE:
<223> OTHER INFORMATION: PCR primer

<400> SEQUENCE: 66 gtttttttttt ggattttttgt tttttg                                    26

<210> SEQ ID NO 67
<211> LENGTH: 19
<212> TYPE: DNA
<213> ORGANISM: Artificial sequence
<220> FEATURE:
<223> OTHER INFORMATION: PCR primer

<400> SEQUENCE: 67 gtttttttcgg ggcggtttc                                             19

<210> SEQ ID NO 68
<211> LENGTH: 31
<212> TYPE: DNA
<213> ORGANISM: Artificial sequence
<220> FEATURE:
<223> OTHER INFORMATION: PCR primer

<400> SEQUENCE: 68
ttttgttttg ttatttttg tttttggttt t                                 31

<210> SEQ ID NO 69
<211> LENGTH: 29
<212> TYPE: DNA
<213> ORGANISM: Artificial sequence
<220> FEATURE:
<223> OTHER INFORMATION: PCR primer

<400> SEQUENCE: 69
cgtttcgtta ttttttgttt tcggttttc                                   29

<210> SEQ ID NO 70
<211> LENGTH: 23
<212> TYPE: DNA
<213> ORGANISM: Artificial Sequence
<220> FEATURE:
<223> OTHER INFORMATION: PCR primer

<400> SEQUENCE: 70
gtttggttgt tgtttattgg ttg                                         23

<210> SEQ ID NO 71
<211> LENGTH: 22
<212> TYPE: DNA
<213> ORGANISM: Artificial sequence
<220> FEATURE:
<223> OTHER INFORMATION: PCR primer

<400> SEQUENCE: 71
cctaaactca caaccaact ca                                           22
```

```
<210> SEQ ID NO 72
<211> LENGTH: 21
<212> TYPE: DNA
<213> ORGANISM: Artificial sequence
<220> FEATURE:
<223> OTHER INFORMATION: PCR primer

<400> SEQUENCE: 72
tgcgagcgtt tttttaaatg c                                              21

<210> SEQ ID NO 73
<211> LENGTH: 20
<212> TYPE: DNA
<213> ORGANISM: Artificial sequence
<220> FEATURE:
<223> OTHER INFORMATION: PCR primer

<400> SEQUENCE: 73
taaactcgca aaccaactcg                                                20

<210> SEQ ID NO 74
<211> LENGTH: 22
<212> TYPE: DNA
<213> ORGANISM: Artificial sequence
<220> FEATURE:
<223> OTHER INFORMATION: PCR primer

<400> SEQUENCE: 74
ttaataggaa gagtggatag tg                                             22

<210> SEQ ID NO 75
<211> LENGTH: 24
<212> TYPE: DNA
<213> ORGANISM: Artificial sequence
<220> FEATURE:
<223> OTHER INFORMATION: PCR primer

<400> SEQUENCE: 75
tctataaatt actaaatctc ttca                                           24

<210> SEQ ID NO 76
<211> LENGTH: 21
<212> TYPE: DNA
<213> ORGANISM: Artificial sequence
<220> FEATURE:
<223> OTHER INFORMATION: PCR primer

<400> SEQUENCE: 76
ttaataggaa gagcggatag c                                              21

<210> SEQ ID NO 77
<211> LENGTH: 23
<212> TYPE: DNA
<213> ORGANISM: Artificial sequence
<220> FEATURE:
<223> OTHER INFORMATION: PCR primer

<400> SEQUENCE: 77
ctataaatta ctaaatctct tcg                                            23

<210> SEQ ID NO 78
<211> LENGTH: 25
<212> TYPE: DNA
<213> ORGANISM: Artificial sequence
<220> FEATURE:
<223> OTHER INFORMATION: PCR primer
```

```
<400> SEQUENCE: 78
taattttagg ttagagggtt attgt                                      25

<210> SEQ ID NO 79
<211> LENGTH: 20
<212> TYPE: DNA
<213> ORGANISM: Artificial sequence
<220> FEATURE:
<223> OTHER INFORMATION: PCR primer

<400> SEQUENCE: 79
cacaaccaat caacaacaca                                            20

<210> SEQ ID NO 80
<211> LENGTH: 22
<212> TYPE: DNA
<213> ORGANISM: Artificial sequence
<220> FEATURE:
<223> OTHER INFORMATION: PCR primer

<400> SEQUENCE: 80
ttaggttaga gggttatcgc gt                                         22

<210> SEQ ID NO 81
<211> LENGTH: 23
<212> TYPE: DNA
<213> ORGANISM: Artificial sequence
<220> FEATURE:
<223> OTHER INFORMATION: PCR primer

<400> SEQUENCE: 81
taactaaaaa ttcacctacc gac                                        23

<210> SEQ ID NO 82
<211> LENGTH: 27
<212> TYPE: DNA
<213> ORGANISM: Artificial sequence
<220> FEATURE:
<223> OTHER INFORMATION: PCR primer

<400> SEQUENCE: 82
ggaggatagt tggattgagt taatgtt                                    27

<210> SEQ ID NO 83
<211> LENGTH: 21
<212> TYPE: DNA
<213> ORGANISM: Artificial sequence
<220> FEATURE:
<223> OTHER INFORMATION: PCR primer

<400> SEQUENCE: 83
caaatccctc ccaaacacca a                                          21

<210> SEQ ID NO 84
<211> LENGTH: 24
<212> TYPE: DNA
<213> ORGANISM: Artificial sequence
<220> FEATURE:
<223> OTHER INFORMATION: PCR primer

<400> SEQUENCE: 84
ggatagtcgg atcgagttaa cgtc                                       24

<210> SEQ ID NO 85
<211> LENGTH: 16
```

```
<212> TYPE: DNA
<213> ORGANISM: Artificial sequence
<220> FEATURE:
<223> OTHER INFORMATION: PCR primer

<400> SEQUENCE: 85
ccctcccaaa cgccga                                                    16

<210> SEQ ID NO 86
<211> LENGTH: 29
<212> TYPE: DNA
<213> ORGANISM: Artificial sequence
<220> FEATURE:
<223> OTHER INFORMATION: PCR primer

<400> SEQUENCE: 86
tttgtgtttt gatgtttgta ggtttttgt                                      29

<210> SEQ ID NO 87
<211> LENGTH: 28
<212> TYPE: DNA
<213> ORGANISM: Artificial sequence
<220> FEATURE:
<223> OTHER INFORMATION: PCR primer

<400> SEQUENCE: 87
aactccacac tcttccaaaa acaaaaca                                       28

<210> SEQ ID NO 88
<211> LENGTH: 23
<212> TYPE: DNA
<213> ORGANISM: Artificial sequence
<220> FEATURE:
<223> OTHER INFORMATION: PCR primer

<400> SEQUENCE: 88
tttcgacgtt cgtaccttttt cgc                                           23

<210> SEQ ID NO 89
<211> LENGTH: 22
<212> TYPE: DNA
<213> ORGANISM: Artificial sequence
<220> FEATURE:
<223> OTHER INFORMATION: PCR primer

<400> SEQUENCE: 89
gcactcttcc gaaaacgaaa cg                                             22

<210> SEQ ID NO 90
<211> LENGTH: 22
<212> TYPE: DNA
<213> ORGANISM: Artificial sequence
<220> FEATURE:
<223> OTHER INFORMATION: PCR primer

<400> SEQUENCE: 90
ggggttgagg tttttttgtta gt                                            22

<210> SEQ ID NO 91
<211> LENGTH: 23
<212> TYPE: DNA
<213> ORGANISM: Artificial sequence
<220> FEATURE:
<223> OTHER INFORMATION: PCR primer

<400> SEQUENCE: 91
```
ttcacaacct caaatctact tca                                   23

<210> SEQ ID NO 92
<211> LENGTH: 21
<212> TYPE: DNA
<213> ORGANISM: Artificial sequence
<220> FEATURE:
<223> OTHER INFORMATION: PCR primer

<400> SEQUENCE: 92
gggttgaggt tttttgttag c                                     21

<210> SEQ ID NO 93
<211> LENGTH: 20
<212> TYPE: DNA
<213> ORGANISM: Artificial sequence
<220> FEATURE:
<223> OTHER INFORMATION: PCR primer

<400> SEQUENCE: 93
ctacttcgcc taacctaacg                                       20

<210> SEQ ID NO 94
<211> LENGTH: 25
<212> TYPE: DNA
<213> ORGANISM: Artificial sequence
<220> FEATURE:
<223> OTHER INFORMATION: PCR primer

<400> SEQUENCE: 94
ggtgttgtta aatgtaaata atttg                                 25

<210> SEQ ID NO 95
<211> LENGTH: 22
<212> TYPE: DNA
<213> ORGANISM: Artificial sequence
<220> FEATURE:
<223> OTHER INFORMATION: PCR primer

<400> SEQUENCE: 95
aaaaaaaaac acctaaaact ca                                    22

<210> SEQ ID NO 96
<211> LENGTH: 21
<212> TYPE: DNA
<213> ORGANISM: Artificial sequence
<220> FEATURE:
<223> OTHER INFORMATION: PCR primer

<400> SEQUENCE: 96
aatcgaattt gtcgtcgttt c                                     21

<210> SEQ ID NO 97
<211> LENGTH: 25
<212> TYPE: DNA
<213> ORGANISM: Artificial sequence
<220> FEATURE:
<223> OTHER INFORMATION: PCR primer

<400> SEQUENCE: 97
aaataaataa ataaaaaaaa acgcg                                 25

<210> SEQ ID NO 98
<211> LENGTH: 26
<212> TYPE: DNA
<213> ORGANISM: Artificial sequence

```
<220> FEATURE:
<223> OTHER INFORMATION: PCR primer

<400> SEQUENCE: 98
gaattgagat gattttaatt ttttgt                                          26

<210> SEQ ID NO 99
<211> LENGTH: 22
<212> TYPE: DNA
<213> ORGANISM: Artificial sequence
<220> FEATURE:
<223> OTHER INFORMATION: PCR primer

<400> SEQUENCE: 99
ctaaaaccat caccoctaaa ca                                              22

<210> SEQ ID NO 100
<211> LENGTH: 23
<212> TYPE: DNA
<213> ORGANISM: Artificial sequence
<220> FEATURE:
<223> OTHER INFORMATION: PCR primer

<400> SEQUENCE: 100
ttgagacgat tttaattttt tgc                                             23

<210> SEQ ID NO 101
<211> LENGTH: 20
<212> TYPE: DNA
<213> ORGANISM: Artificial sequence
<220> FEATURE:
<223> OTHER INFORMATION: PCR primer

<400> SEQUENCE: 101
aaaaccatca cccctaaacg                                                 20

<210> SEQ ID NO 102
<211> LENGTH: 22
<212> TYPE: DNA
<213> ORGANISM: Artificial sequence
<220> FEATURE:
<223> OTHER INFORMATION: PCR primer

<400> SEQUENCE: 102
gagtggttag aggaatttag gt                                              22

<210> SEQ ID NO 103
<211> LENGTH: 24
<212> TYPE: DNA
<213> ORGANISM: Artificial sequence
<220> FEATURE:
<223> OTHER INFORMATION: PCR primer

<400> SEQUENCE: 103
ctaaaaaaac aaacaaaaca tcca                                            24

<210> SEQ ID NO 104
<211> LENGTH: 20
<212> TYPE: DNA
<213> ORGANISM: Artificial sequence
<220> FEATURE:
<223> OTHER INFORMATION: PCR primer

<400> SEQUENCE: 104
gtggttagag gaatttaggc                                                 20
```

<210> SEQ ID NO 105
<211> LENGTH: 19
<212> TYPE: DNA
<213> ORGANISM: Artificial sequence
<220> FEATURE:
<223> OTHER INFORMATION: PCR primer

<400> SEQUENCE: 105
aaaacgaacg aaacgtccg                                          19

<210> SEQ ID NO 106
<211> LENGTH: 21
<212> TYPE: DNA
<213> ORGANISM: Artificial sequence
<220> FEATURE:
<223> OTHER INFORMATION: PCR primer

<400> SEQUENCE: 106
acttccatta aaaacaacta c                                       21

<210> SEQ ID NO 107
<211> LENGTH: 23
<212> TYPE: DNA
<213> ORGANISM: Artificial sequence
<220> FEATURE:
<223> OTHER INFORMATION: PCR primer

<400> SEQUENCE: 107
caaccccaaa cccacaacca taa                                     23

<210> SEQ ID NO 108
<211> LENGTH: 22
<212> TYPE: DNA
<213> ORGANISM: Artificial sequence
<220> FEATURE:
<223> OTHER INFORMATION: PCR primer

<400> SEQUENCE: 108
gacccccgaa ccgcgaccct aa                                      22

<210> SEQ ID NO 109
<211> LENGTH: 23
<212> TYPE: DNA
<213> ORGANISM: Artificial sequence
<220> FEATURE:
<223> OTHER INFORMATION: PCR primer

<400> SEQUENCE: 109
ttacaaaaaa ccttccaaat aca                                     23

<210> SEQ ID NO 110
<211> LENGTH: 22
<212> TYPE: DNA
<213> ORGANISM: Artificial sequence
<220> FEATURE:
<223> OTHER INFORMATION: PCR primer

<400> SEQUENCE: 110
tacaaaaaac cttccgaata cg                                      22

<210> SEQ ID NO 111
<211> LENGTH: 23
<212> TYPE: DNA
<213> ORGANISM: Artificial sequence
<220> FEATURE:
<223> OTHER INFORMATION: PCR primer

```
<400> SEQUENCE: 111
tttattccaa cttcttcact tca                                              23

<210> SEQ ID NO 112
<211> LENGTH: 19
<212> TYPE: DNA
<213> ORGANISM: Artificial sequence
<220> FEATURE:
<223> OTHER INFORMATION: PCR primer

<400> SEQUENCE: 112
ttccgacttc ttcgcttcg                                                   19

<210> SEQ ID NO 113
<211> LENGTH: 21
<212> TYPE: DNA
<213> ORGANISM: Artificial sequence
<220> FEATURE:
<223> OTHER INFORMATION: PCR primer

<400> SEQUENCE: 113 cccccaaaa accccacctc a                                                 21

<210> SEQ ID NO 114
<211> LENGTH: 17
<212> TYPE: DNA
<213> ORGANISM: Artificial sequence
<220> FEATURE:
<223> OTHER INFORMATION: PCR primer

<400> SEQUENCE: 114
ccgaaaaccc cgcctcg                                                     17
```

DIFFERENTIALLY METHYLATED SEQUENCES IN PANCREATIC CANCER

RELATED APPLICATIONS

This application claims priority under 35 U.S.C. §119(e) to U.S. Provisional Application Ser. No. 60/271,268, filed Feb. 23, 2001, which is herein incorporated by reference in its entirety.

FIELD OF THE INVENTION

The present invention relates generally to the regulation of gene expression and more specifically to a method of determining the DNA methylation status of CpG sites in a given locus and correlating the methylation status with the presence of a cell proliferative disorder.

BACKGROUND OF THE INVENTION

DNA methylases transfer methyl groups from the universal methyl donor S-adenosyl methionine to specific sites on the DNA. Several biological functions have been attributed to the methylated bases in DNA. The most established biological function for methylated DNA is the protection of DNA from digestion by cognate restriction enzymes. The restriction modification phenomenon has, so far, been observed only in bacteria. Mammalian cells, however, possess a different methylase that exclusively methylates cytosine residues that are 5' neighbors of guanine (CpG). This modification of cytosine residues has important regulatory effects on gene expression, especially when involving CpG rich areas, known as CpG islands, located in the promoter regions of many genes.

Methylation has been shown by several lines of evidence to play a role in gene activity, cell differentiation, tumorigenesis, X-chromosome inactivation, genomic imprinting and other major biological processes (Razin, A., H., and Riggs, R. D. eds. in *DNA Methylation Biochemistry and Biological Significance,* Springer-Verlag, New York, 1984). In eukaryotic cells, methylation of cytosine residues that are immediately 5' to a guanosine, occurs predominantly in CG poor regions (Bird, A., Nature, 321:209, 1986). In contrast, CpG islands remain unmethylated in normal cells, except during X-chromosome inactivation (Migeon, et al., supra) and parental specific imprinting (Li, et al., Nature, 366:362, 1993) where methylation of 5' regulatory regions can lead to transcriptional repression. De novo methylation of the Rb gene has been demonstrated in a small fraction of retinoblastomas (Sakai, et al., Am. J. Hum. Genet., 48:880, 1991), and recently, a more detailed analysis of the VHL gene showed aberrant methylation in a subset of sporadic renal cell carcinomas (Herman, et al., Proc. Natl. Acad. Sci., U.S.A., 91:9700, 1994). Expression of a tumor suppressor gene can also be abolished by de novo DNA methylation of a normally unmethylated CpG island (Issa, et al., Nature Genet., 7:536, 1994; Herman, et al., supra; Merlo, et al., Nature Med., 1:686, 1995; Herman, et al., Cancer Res., 56:722, 1996; Graff, et al., Cancer Res., 55:5195, 1995; Herman, et al., Cancer Res., 55:4525, 1995).

Human cancer cells typically contain somatically altered nucleic acid, characterized by mutation, amplification, or deletion of critical genes. In addition, the nucleic acid from human cancer cells often displays somatic changes in DNA methylation (E. R. Fearon, et al., Cell, 61:759, 1990; P. A. Jones, et al., Cancer Res., 46:461, 1986; R. Holliday, Science, 238:163, 1987; A. De Bustros, et al., Proc. Natl. Acad. Sci., USA, 85:5693, 1988); P. A. Jones, et al., Adv. Cancer Res., 54:1, 1990; S. B. Baylin, et al., Cancer Cells, 3:383, 1991; M. Makos, et al., Proc. Natl. Acad. Sci., USA, 89:1929, 1992; N. Ohtani-Fujita, et al., Oncogene, 8:1063, 1993). However, the precise role of abnormal DNA methylation in human tumorigenesis has not been established. Aberrant methylation of normally unmethylated CpG islands has been described as a frequent event in immortalized and transformed cells, and has been associated with transcriptional inactivation of defined tumor suppressor genes in human cancers. In the development of colorectal cancers (CRC), a series of tumor suppressor genes (TSG) such as APC, p53, DCC and DPC4 are inactivated by mutations and chromosomal deletions. Some of these alterations result from a chromosomal instability phenotype described in a subset of CRC. Recently, an additional pathway has been shown to be involved in a familial form of CRC, hereditary non-polyposis colorectal cancer. The cancers from these patients show a characteristic mutator phenotype which causes microsatellite instability (MI), and mutations at other gene loci such as TGF-β-RII (Markowitz et al., Science, 268(5215):1336–8, 1995) and BAX. This phenotype usually results from mutations in the mismatch repair (MMR) genes hMSH2 and hMLH1. A subset of sporadic CRC also show MI, but mutations in MMR genes appear to be less frequent in these tumors.

Another molecular defect described in CRC is CpG island (CGI) methylation. CGIs are short sequences rich in the CpG dinucleotide and can be found in the 5' region of about half of all human genes. Methylation of cytosine within 5' CGIs is associated with loss of gene expression and has been seen in physiological conditions such as X chromosome inactivation and genomic imprinting. Aberrant methylation of CGIs has been detected in genetic diseases such as the fragile-X syndrome, in aging cells and in neoplasia. About half of the tumor suppressor genes which have been shown to be mutated in the germline of patients with familial cancer syndromes have also been shown to be aberrantly methylated in some proportion of sporadic cancers, including Rb, VHL, p16, hMLH1, and BRCA1. TSG methylation in cancer is usually associated with (Antequera, et al., Proc. Natl. Acad. Sci. USA, 90:11995–11999, 1993) lack of gene transcription and (Baylin, et al., Adv. Cancer Res., 72:141–196, 1998) absence of coding region mutation. Thus it has been proposed that CGI methylation serves as an alternative mechanism of gene inactivation in cancer.

The causes and global patterns of CGI methylation in human cancers remain poorly defined. Aging could play a factor in this process because methylation of several CGIs could be detected in an age-related manner in normal colon mucosa as well as in CRC. In addition, aberrant methylation of CGIs has been associated with the MI phenotype in CRC as well as specific carcinogen exposures. However, an understanding of aberrant methylation in CRC has been somewhat limited by the small number of CGIs analyzed to date. In fact, previous studies have suggested that large numbers of CGIs are methylated in immortalized cell lines, and it is not well understood whether this global aberrant methylation is caused by the cell culture conditions or whether they are an integral part of the pathogenesis of cancer.

Most of the methods developed to date for detection of methylated cytosine depend upon cleavage of the phosphodiester bond alongside cytosine residues, using either methylation-sensitive restriction enzymes or reactive chemicals such as hydrazine which differentiate between cytosine and its 5-methyl derivative. Genomic sequencing protocols which identify a 5-MeC residue in genomic DNA as a site that is not cleaved by any of the Maxam Gilbert sequencing reactions have also been used, but still suffer disadvantages such as the requirement for large amount of genomic DNA and the difficulty in detecting a gap in a sequencing ladder which may contain bands of varying intensity.

Mapping of methylated regions in DNA has relied primarily on Southern hybridization approaches, based on the inability of methylation-sensitive restriction enzymes to cleave sequences which contain one or more methylated CpG sites. This method provides an assessment of the overall methylation status of CpG islands, including some quantitative analysis, but is relatively insensitive and requires large amounts of high molecular weight DNA.

Another method utilizes bisulfite treatment of DNA to convert all unmethylated cytosines to uracil. The altered DNA is amplified and sequenced to show the methylation status of all CpG sites. However, this method is technically difficult, labor intensive and without cloning amplified products, it is less sensitive than Southern analysis, requiring approximately 10% of the alleles to be methylated for detection.

Identification of the earliest genetic changes in tumorigenesis is a major focus in molecular cancer research. Diagnostic approaches based on identification of these changes are likely to allow implementation of early detection strategies and novel therapeutic approaches targeting these early changes might lead to more effective cancer treatment.

About half of all human genes have 5' CpG islands and these islands are usually associated with the 5' regulatory regions of genes (Antequera, et al., Proc. Natl. Acad. Sci. USA 90:11995–11999, 1993). The 5' CpG islands of most nonimprinted genes are thought to remain unmethylated in normal cells but may become methylated during aging or tumorigenesis. Through interactions between methyl CpG binding proteins, histones and histone deacetylase, 5' CpG island methylation can contribute to changes in chromatin that cause transcriptional silencing (Baylin, et al., Adv. Cancer Res. 72:141–196, 1998). Promoter methylation is implicated in the transcriptional silencing of tumor suppressor and mismatch repair genes (e.g. p16, Rb, VHL, hMLH1) in many cancers. Although 13 hypermethylated genes and clones in pancreatic cancers were previously identified (Ueki, et al., Cancer Res. 60:1835–1839, 2000), there almost certainly are others. Costello et al. have estimated that ~400 genes are aberrantly methylated in cancers and have found evidence for tumor-specific pattern of methylation (Costello, et al., Nat. Genet. 24:132–138, 2000). A better description of the pattern of DNA methylation abnormalities in cancer may improve an understanding of the role of DNA methylation in tumorigenesis and identification of differentially methylated CpG islands in cancer may lead to the discovery of novel genes with tumor suppressor properties. Finally, identified genes or loci could be utilized as cancer-specific markers for the early detection of cancer (Belinsky, et al., Proc. Natl. Acad. Sci. USA 95:11891–11896, 1998).

Pancreatic cancer is the fourth leading cause of cancer death in men and in women and each year ~28,000 Americans die of the disease (Greenlee, et al., CA Cancer J. Clin. 50:7–33, 2000). Frequent genetic changes such as mutational activation of the K-ras oncogene and inactivation of the p16, DPC4, p53, MKK4, STK11, TGFBR2, and TGFBR1 tumor suppressor genes have been described in pancreatic cancer (Goggins, et al., Ann. Oncol. 10:4–8, 1999, Rozenblum, et al., Cancer Res. 57:1731–1734, 1997). Although multiple tumor suppressor pathways have been shown to play a role in pancreatic carcinogenesis, little is known about the contribution of DNA methylation to inactivation of genes in these pathways. Recently, a novel technique, methylated CpG island amplification (MCA), was developed to enrich for methylated CpG rich sequences. MCA coupled with RDA (MCA/RDA) can recover CpG islands differentially methylated in cancer cells (Toyota, et al., Cancer Res. 59:2307–2312, 1997).

SUMMARY OF THE INVENTION

The present invention is based on the finding that several genes are newly identified as being differentially methylated in cancer. This seminal discovery is useful for cancer screening, risk-assessment, prognosis, minimal-residual disease identification, staging and identification of therapeutic targets. The identification of new genes that are methylated in cancer, aging or diseases associated with aging increases the likelihood of finding genes methylated in a particular cancer; increases the sensitivity and specificity of methylation detection; allows methylation profiling using multiple genes; and allows identification of new targets for therapeutic intervention. The invention also provides a newly identified gene that is a target for hypermethylation in human tumors.

In one embodiment, there are provided methods for detecting a cellular proliferative disorder in a subject. The subject may have or be at risk of having a cellular proliferative disorder. The method of the invention is useful for diagnostic as well as prognostic analyses. One method for detecting a cellular proliferative disorder in a subject includes contacting a nucleic acid-containing specimen from the subject with an agent that provides a determination of the methylation state of at least one gene or associated regulatory region of the gene; and identifying aberrant methylation of regions of the gene or regulatory region, wherein aberrant methylation is identified as being different when compared to the same regions of the gene or associated regulatory region in a subject not having the cellular proliferative, thereby detecting a cellular proliferative disorder in the subject. The method includes multiplexing by utilizing a combination of primers for more than one loci, thereby providing a methylation "profile" for more than one gene or regulatory region.

For the first time, the invention provides methylated forms of genes and/or their associated regulatory sequences referred to herein as MICP 1–42. MICP39–42 have no homology to known human sequences. Eleven clones matched human genes (MICP1–11); 10 clones matched human ESTs (MICP12–21); 5 clones matched human CpG islands (MICP22–26); and 12 clones matched human genome sequences (MICP27–38). (see Table 1 as reference).

Invention methods include determining, in a nucleic acid-containing specimen taken from a subject, the methylation state of a gene or regulatory sequences associated therewith, wherein the expression or non-expression of the gene is associated with the presence of the cellular proliferative disorder, and identifying as having a cellular proliferative disorder a subject that has aberrant methylation of regions of the gene or associated regulatory sequences when compared to the same regions of the gene in a subject not having the cellular proliferative disorder. In one aspect of this embodiment, the methylated regions of the gene and associated regulatory sequences are contained within CpG islands (i.e., CpG rich regions). In particular, the aberrant methylation typically includes hypermethylation as compared with the same regions of the gene or regulatory sequences in a subject not having the cellular proliferative disorder.

Determining the methylation state of the gene includes contacting the nucleic acid-containing specimen with an agent that modifies unmethylated cytosine, amplifying a CpG-containing nucleic acid in the specimen by means of CpG-specific oligonucleotide primers, wherein the oligonucleotide primers distinguish between modified methylated and nonmethylated nucleic acid, and detecting the methylated nucleic acid based on the presence or absence of amplification products produced in said amplifying step. The method includes optionally contacting the amplification products with a methylation sensitive restriction endonuclease. Other methods for determining methylation status of a gene and/or regulatory sequences are well known in the art and are described more fully herein.

In another embodiment of the present invention there is provided a kit useful for the detection of a cellular proliferative disorder in a subject having or at risk for having a cellular proliferative disorder. Invention kits include a carrier means compartmentalized to receive a sample, one or more containers comprising a first container containing a reagent which modifies unmethylated cytosine and a second container containing primers for amplification of a CpG-containing nucleic acid, wherein the primers distinguish between modified methylated and nonmethylated nucleic acid, and optionally, a third container containing a methylation sensitive restriction endonuclease. In a preferred embodiment, the cell proliferative disorder is pancreatic carcinoma.

To identify CpG islands differentially methylated in pancreatic adenocarcinoma, methylated CpG island amplification (MCA) was used, coupled with representational difference analysis (MCA/RDA). Clones differentially methylated (termed MICP, methylated in carcinoma of the pancreas) were isolated in a panel of 8 pancreatic cancer cell lines compared to normal pancreas. 95% of these clones were CpG islands and among these clones were 5' CpG islands of several known genes, including Cyclin G and Preproenkephalin (ppENK, encoding [Met5]-enkephalin). Seven of the clones (Cyclin G, ppENK, MICP20, 23, 33, 35 and 36) were not methylated in 14 normal pancreata by MSP while 15 primary pancreatic adenocarcinomas were methylated in 7%, 87%, 13%, 53%, 33%, 40% and 0% of cases, respectively. Two of the 5 chronic pancreatitis specimens harbored methylation of three (Cyclin G, ppENK and MICP23) and one (ppENK) clones, respectively. There was no identification of methylation of MICP33 and 35 in any normal gastrointestinal tissues tested. Three clones (ppENK, MICP20 and 23) were variably methylated in normal gastric, duodenal and colonic mucosae. Aberrant methylation of Cyclin G and ppENK in methylated pancreatic cancer cell lines was associated with transcriptional silencing that was reversible with 5-aza-2'-deoxycytidine treatment.

These data indicate that multiple CpG islands undergo de novo methylation during pancreatic carcinogenesis. Methylation of some CpG islands is cancer-specific while others show tissue-specific patterns of methylation.

BRIEF DESCRIPTION OF THE FIGURES

FIGS. 6a–6i show the nucleic acid sequence for SEQ ID NO: 1–42.

DETAILED DESCRIPTION OF THE INVENTION

Figure 1:
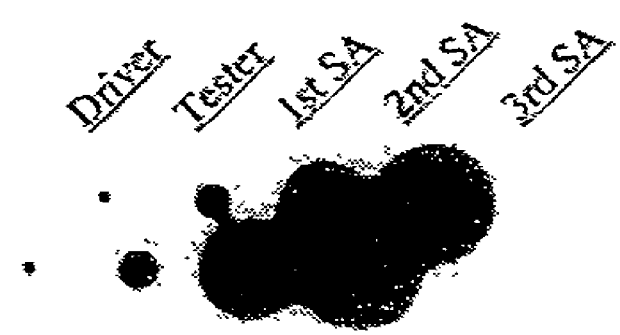
FIG. 1 shows the representative results of MCIPs isolated by MCA/RDA. Dot blot analysis. 1A, An example of kinetic enrichment of methylated sequences by RDA. MCA products from the driver and the tester (PL8) and the PCR products from first (1st SA), second (2nd SA) and third (3rd SA) competitive hybridization/selective amplification were blotted onto the membrane and hybridized with a labeled Cyclin G probe. 1B, Dot blot analysis using MICPs isolated from MCA/RDA as probes. First three MICPs were hybridized only to the tester (either PL3 or PL8), whereas the next three MICPs were weakly hybridized to the driver as well as the tester.

It has been determined that an aberrant methylation state of nucleic acids in certain genes, particularly regulatory sequences, is diagnostic for the presence or potential development of a cellular proliferative disorder in subjects bearing the aberrantly methylated nucleic acids. More particularly, the hypermethylation of certain nucleotides localized in CpG islands has been shown to affect the expression of genes associated with the CpG islands; typically such hypermethylated genes have reduced or abolished expression, primarily due to down-regulated transcription. Using a recently developed PCR-based technique called methylated CpG island amplification (MCA), several nucleic acid molecules aberrantly methylated in pancreatic cancer cells line were identified.

Of the 42 unique clones isolated using MCA/RDA, seven (Cyclin G, ppENK, MICP20, 23, 33, 35 and 36) were CpG islands aberrantly methylated in pancreatic carcinoma compared to normal pancreas. Indeed, none of these 7 clones, were methylated in a panel of normal pancreata using the highly sensitive method of MSP. Two of these seven clones corresponded to the 5' CpG island of the genes ppENK and Cyclin G. ppENK encodes opioid growth factor, also known as [Met5]-enkephalin. This opioid peptide induces apoptosis in lung cancer cell lines (Maneckjee & Minna, Cell Growth Differ. 5:1033–1040, 1994) and several studies have demonstrated that this peptide has a negative growth regulatory effect on various kinds of cancers, including pancreatic cancer (Zagon, et al., Int. J. Oncol. 14:577–584, 1999). Aberrant methylation of the 5' CpG island of ppENK was found in 87% of primary pancreatic carcinomas. Hypermethylation was associated with transcriptional silencing of this gene in pancreatic cancer cell lines. Although a low level of methylation in other normal mucosae by MSP was also observed, these results indicate that de novo methylation of 5' CpG islands and transcriptional repression of ppENK might contribute to pancreatic carcinogenesis.

Cyclin G is a target for transcriptional activation by p53 (Okamoto, et al., Embo. J. 13:48616–4822, 1994). Conflicting functions for Cyclin G have been reported. When overexpressed Cyclin G is associated with cell growth in vitro (Smith, et al., Exp. Cell. Res. 230:61–68, 1997), while increased expression of Cyclin G also augments apoptosis of multiple cancer cell lines in response to different stimuli (Okamoto & Prives, Oncogene 18:4606–4615, 1999). The data demonstrate the association between hypermethylation of the 5' CpG island of Cyclin G and its transcriptional repression in the pancreatic cancer cell line PL8 (FIG. 4C), suggesting that Cyclin G could have been selected for silencing because of tumor suppressive functions. These data extend previous findings demonstrating aberrant methylation of multiple cancer-related genes including p16 and HMLH1 in pancreatic cancer (Ueki, et al., Cancer Res. 60:1835–1839, 2000).

Methylation of several clones in pancreata with chronic pancreatitis was also observed. Two of the 5 pancreata with chronic pancreatitis harbored aberrant methylation and one of these two pancreata contained a PanIN lesion and this latter sample displayed methylation of 3 clones. Previous studies demonstrated that chronic pancreatitis is a significant risk factor of development of pancreatic cancer (Lowenfels, et al., N. Engl. J. Med. 328:1433–1437, 1993) and duct lesions (PanIN) often found in chronic pancreatitis are considered as the precursors of infiltrating pancreatic carcinoma (Hruban, et al., Clin. Cancer Res. 6:2969–2972, 2000). The presence of aberrant methylation in DNA from chronic pancreatitis suggests that de novo methylation of CpG islands may be an early event in pancreatic cancer development in this setting. Additional studies are needed to determine the role and the timing of de novo methylation of CpG islands in progression model of pancreatic cancer (Hruban, et al., Clin. Cancer Res. 6:2969–2972, 2000). The absence of methylated templates of MICP33 and 35 in any normal tissue examined raises the possibility that MSP could be used to detect aberrant methylation of these clones in clinical samples such as stool, blood, or pancreatic fluid, for the early detection of pancreatic cancers.

Three additional known genes containing methylated 5' CpG islands in pancreatic cancers were identified (GAD1, ECEL1 and PAX5). These genes were isolated by MCA/RDA because relatively fewer DNA templates were methylated in normal pancreas. Some genes that are methylated in cancer and in only a small percentage of normal cells may appear to undergo selection during carcinogenesis (Salem, et al., Cancer Res. 60:2473–2476, 2000), but are merely unselected epigenetic markers of stem cells that have evolved to cancers by other clonal selection events. This phenomenon is important to be aware of when studying methylation in human cancer and makes it much more difficult to assign causality to methylation phenomena in cancers compared to genetic events such as homozygous deletion. For normally unmethylated genes whose function is well characterized such as hMLH1, or for genes that are methylated as a second hit for a tumor suppressor gene (e.g. VHL, E-cadherin), or for tumor suppressor genes alternatively targeted by genetic and epigenetic inactivation (e.g. p16 and RB) (Baylin, et al., Adv. Cancer Res. 72:141–196, 1998), the biological significance of "aberrant methylation" is well accepted. As additional genes are identified that are methylated in pancreatic cancer, it will be important to rule out low-level methylation using sensitive techniques such as MSP (Herman, et al., Proc. Natl. Acad. Sci. USA 93:9821–9826, 1996) before such genes are accepted as having undergone selection through methylation.

Three CpG islands that were differentially methylated in pancreatic cancer but were not located within 5' regions of their corresponding genes were also identified, CSX, MCT3 and ICAM5. The role of hypermethylation of non-5' CpG islands need to be defined, but recent studies have shown that aberrant methylation in cancer is not confined to the 5' region but can occur in internal exons and 3' regions of genes (Costello, et al., Nat. Genet. 24:132–138, 2000, Liang, et al., Genomics 53:260–268, 1998). It is probable that several of the unknown clones identified are genes whose expression is repressed by aberrant methylation. For example, GRAIL and GENSCAN programs suggest putative coding exons downstream of MICP23 and MICP33.

Figure 3:
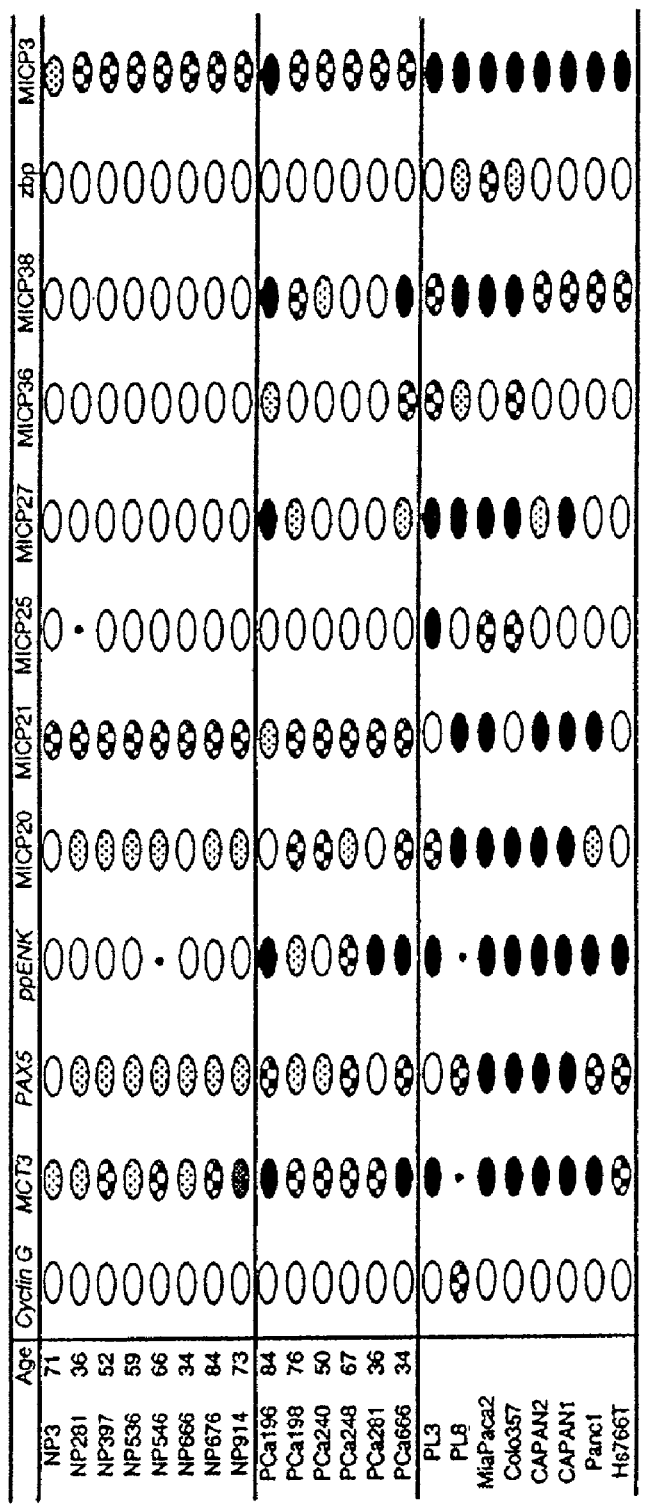
FIG. 3 shows a summary of the average level of methylation of selected MCA/RDA MICPs by bisulfite-modified genomic sequencing. The specimen number and the age of the patients are in the left column. Empty oval, 0–10% methylation; white oval with black dots, 11–30% methylation; black oval with white dots, 31–70% methylation; black oval, 71–100% methylation; ., not determined, NP, normal pancrease; PCa, primary pancreatic adenocarcinonma.

In addition to identifying CpG islands with cancer-related methylation, CpG islands that were methylated in both normal pancreata and neoplastic tissues were isolated. Methylation of non-neoplastic colorectal (Ahuja, et al., Cancer Res. 58:5489–5494, 1998, Toyota, et al., Proc. Natl. Acad. Sci. USA 96:8681–8686, 1999), bladder and prostate tissues (Liang, et al., Genomics 53:260–268, 1998) has been observed for several genes and CpG islands. Methylation in normal tissues that is not the result of imprinting is frequently "age-related." This has been best shown in the colonic mucosa for genes such as ER (Ahuja, et al., Cancer Res. 58:5489–5494, 1998, Toyota, et al., Proc. Natl. Acad. Sci. USA 96:8681–8686, 1999). However, normal pancreata used in this study were obtained from 14 patients (mean age of 62) and for at least 5 of these clones there was no evidence of age-related methylation (FIG. 3). This suggests that the aberrant methylation observed in the pancreatic cancers in this study is not simply a function of age. Some of the clones listed in Table 1 could undergo age-related methylation, but to demonstrate this would require many more normal pancreata. Methylation of ppENK, MICP20 and 23 in a significant percentage of the DNA templates within normal gastric, duodenal and colonic mucosae highlights the tissue specific nature of DNA methylation. This low level methylation of different normal tissues might also explain some of the tumor-specific methylation patterns observed by others (Costello, et al., Nat. Genet. 24:132–138, 2000). The data indicate that there are tissue-specific methylation patterns in normal tissues (Liang, et al., Genomics 53:260–268, 1998) and age-related methylation changes are probably restricted to certain genes and/or tissues (Ahuja, et al., Cancer Res. 58:5489–5494, 1998).

In this study, the MCA/RDA technique was modified and these modifications may have improved the efficiency of the MCA/RDA technique. Betaine was included in the PCR reaction and amplified the methylated templates under a higher annealing temperature (77° C.). The combination of betaine and DMSO can uniformly amplify a mixture of DNA with different GC content (Baskaran, et al., Genome Res. 6:633–638, 1996). These modifications might have enhanced the amplification of distinct clones instead of Alu repetitive sequences that accounted for 60% of the recovered clones using the original protocol (Toyota, et al., Cancer Res. 59:2307–2312, 1997). The subtractive and kinetic enrichment of differentially methylated sequence by RDA as shown in this study (FIG. 1A) may have advantages over other techniques to isolate differentially methylated sequences between normal tissue and cancer (Costello, et al., Nat. Genet. 24:132–138, 2000, Liang, et al., Genomics 53:260–268, 1998). MCA/RDA, however, has limitations for identifying differentially methylated sequences. First, MCA only detects differentially methylated sequences with two restriction enzyme sites (Smal in this study). Second, MCA/RDA not only identifies absolute differences in methylation between the tester and the driver, it also will identify methylated sequences both in the tester and the driver if for example, there is low level methylation in the driver (normal pancreas). Third, some clones that appeared to be unmethylated by dot-blot hybridization were indeed methylated by bisulfite sequencing in normal pancreata (MICP 15, FIG. 1B and FIG. 4C). Finally, even if bisulfite sequencing suggests that there is no methylation of a clone in normal pancreata, it is important to rule out low-level methylation in normal tissues using a sensitive technique, such as MSP.

The results indicate that aberrant methylation of CpG islands is a common event in pancreatic carcinogenesis. Some de novo methylated CpG islands could serve as cancer-specific markers while others reflect tissue specific pattern of DNA methylation.

Methylated nucleic acid sequences are also provided. For the first time, the present invention provides methylated chemical structures for MICP 1–42 (see Table 1). One of skill in the art can now readily locate the CpG-rich sequences associated with these genes and identify such methylated forms of the genes/regulatory sequences by methods described herein (The gene sequences can be identified in a gene database found on the world wide web, at the url "ncbi.nim.nih.gov/UniGene/index.html"). The invention provides CpG-rich regions from the above genes as set forth in SEQ ID Nos 1–42, equivalent to MICP 1–42, respectively.

The term "polynucleotide" or "nucleic acid sequence" refers to a polymeric form of nucleotides at least 10 bases in length. An "isolated polynucleotide" is a polynucleotide that is not immediately contiguous with both of the coding sequences with which it is immediately contiguous (one on the 5' end and one on the 3' end) in the naturally occurring genome of the organism from which it is derived. Thus, an isolated polynucleotide may include a coding region with its associated regulatory sequences. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. Specifically, methylated forms of nucleotides in a polynucleotide sequence are also included. The term includes single and double forms of DNA.

As will be understood by those of skill in the art, when the sequence is RNA, the deoxynucleotides A, G, C, and T of SEQ ID NO: 1–42, are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes polypeptides encoded by SEQ ID NO: 1–42. The term "selectively hybridize" refers to hybridization under moderately or highly stringent conditions (See, Sambrook, as cited herein) which excludes non-related nucleotide sequences.

The nucleic acid sequence includes the disclosed sequence and sequences that encode conservative variations of the polypeptides encoded by polynucleotides provided herein. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Nucleic acid sequences of the invention can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cells" is used. Methods of stable transfer, meaning that the foreign DNA is continuously maintained in the host, are known in the art.

In one aspect, the nucleic acid sequences may be inserted into an expression vector. The term "expression vector" refers to a plasmid, virus or other vehicle known in the art that has been manipulated by insertion or incorporation of the sequence of interest genetic sequences. Polynucleotide sequence which encode sequence of interest can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the regulatory or expression control sequences. As used herein, the terms "regulatory sequences" and "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The terms "regulatory sequences" and "expression control sequences" are intended to included, at a minimum, components whose presence can influence expression, and can also include additional components whose presence is advantageous, for example, leader sequences and fusion partner sequences. An example of an expression control sequence includes a promoter.

A "promoter" is a minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see, e.g., Bitter et al., Methods in Enzymology 153:516–544, 1987). For example, when cloning in bacterial systems, inducible promoters such as pL of bacteriophage plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the polynucleotide sequences may be inserted into an expression vector which contains a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., Gene 56:125, 1987), the pMSXND expression vector for expression in mammalian cells (Lee and Nathans, J. Biol. Chem. 263:3521, 1988) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

"Transformation" means a genetic change induced in a cell following incorporation of new DNA (i.e., DNA exogenous to the cell). Where the cell is a mammalian cell, the genetic change is generally achieved by introduction of the DNA into the genome of the cell (i.e., stable).

Thus, a "transformed cell" is a cell into which (or into an ancestor of which) has been introduced, by means of recombinant DNA techniques, a DNA molecule encoding sequence of interest. Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subse quently treated by the CaCl2 method using procedures well known in the art. Alternatively, MgCl2 or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the sequence of interest, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

In one embodiment, the invention provides substantially purified polypeptide encoded by polynucleotide sequences SEQ ID NO: 1–42. The term "substantially purified" as used herein refers to a polypeptide which is substantially free of other proteins, lipids, carbohydrates or other materials with which it is naturally associated. One skilled in the art can purify a polypeptide sequence using standard techniques for protein purification. The substantially pure polypeptide will yield a single major band on a non-reducing polyacrylamide gel. The purity of the polypeptide can also be determined by amino-terminal amino acid sequence analysis.

Minor modifications of the primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity still exists.

The polypeptides of the invention also include dominant negative forms of the invention polypeptide which do not have the biological activity of invention polypeptide sequence. A "dominant negative form" of invention is a polypeptide that is structurally similar to invention polypeptide but does not have wild-type invention function. For example, a dominant-negative invention polypeptide may interfere with wild-type invention function by binding to, or otherwise sequestering, regulating agents, such as upstream or downstream components, that normally interact functionally with the invention polypeptide.

To identify genes differentially methylated in colorectal cancer, methylated CpG island amplification was used followed by representational difference analysis (Razin and Cedar, Cell 17: 473–476, 1994, herein incorporated by reference). One of the clones recovered (MINT31, see U.S. patent application Ser. No. 09/309,175, incorporated by reference herein in its entirety) mapped to human chromosome 17q21 using a radiation hybrid panel. A Blast search revealed this fragment to be completely identical to part of a BAC clone (Genbank: AC004590) sequenced by high throughput genomic sequencing. The region surrounding MINT31 fulfills the criteria of a CpG island: GC content 0.67, CpG/GpC ratio 0.78 and a total of 305 CpG sites in a 4 kb region. Using this CpG island and 10 kb of flanking sequences in a Blast analysis, several regions highly homologous to the rat T-type calcium channel gene, CACNA1G, were identified (Perez-Reyes et al., Nature 391: 896–900. 1998, herein incorporated by reference). Several ESTs were also identified in this region. Using Genscan, 2 putative coding sequences (G1, and G2) were identified. Blastp analysis revealed that G1 has a high homology to the EH-domain-binding protein, epsin, while G2 is homologous to a C. elegans hypothetical protein (accession No. 2496828).

Due to the clear correlation between methylation of CpG islands and cellular proliferative disorders, in another embodiment of the present invention, there are provided methods for detecting a cellular proliferative disorder in a subject having or at risk for said cellular proliferative disorder. The method includes assaying, in nucleic acid-containing specimen taken from said subject, the methylation state of a gene or its associated regulatory regions, wherein the expression state of the gene or its associated regulatory regions is associated with the presence of the cellular proliferative disorder, and identifying as having a cellular proliferative disorder a subject that has aberrant methylation of regions of said gene. The method provides for detecting a cellular proliferative disorder in a subject having or at risk for said cellular proliferative disorder by identifying aberrantly methylation of regions of a gene when compared to the same regions of the gene in a subject not having said cellular proliferative disorder.

The aberrant methylation comprises hypermethylated CpG rich regions (i.e., islands). In one aspect of the present invention, the CpG rich regions are associated with the invention genes gene, and affect the expression thereof in a methylation state-dependent manner.

A "cell proliferative disorder" or "cellular proliferative disorder" is any disorder in which the proliferative capabilities of the affected cells is different from the normal proliferative capabilities of unaffected cells. An example of a cell proliferative disorder is neoplasia. Malignant cells (i.e., cancer) develop as a result of a multistep process. Specific, non-limiting examples of cell proliferative disorders associated with increased methylation of CpG-islands are low grade astrocytoma, anaplastic astrocytoma, glioblastoma, medulloblastoma, gastric cancer, colorectal cancer, colorectal adenoma, acute myelogenous leukemia, lung cancer, renal cancer, pancreatic cancer, leukemia, breast cancer, prostate cancer, endometrial cancer and neuroblastoma.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. For example, the neoplasm may be a head, neck, lung, esophageal, stomach, small bowel, colon, bladder, kidney, or cervical neoplasm. The term "benign" refers to a tumor that is noncancerous, e.g. its cells do not proliferate or invade surrounding tissues. The term "malignant" refers to a tumor that is metastastic or no longer under normal cellular growth control.

A cell proliferative disorder may be an age-associated disorder. Examples of age-associated disorders which are cell proliferative disorders include colon cancer, lung cancer, breast cancer, prostate cancer, and melanoma, amongst others.

A "nucleic acid containing specimen" includes any type of material containing a nucleic acid to be subject to invention methods. The nucleic acid may be contained in a biological sample. Such samples include but are not limited to any bodily fluid, such as a serum, urine, saliva, blood, cerebrospinal fluid, pleural fluid, ascites fluid, sputum, stool, or a biopsy sample.

Samples or specimens include any CpG-rich DNA sequence, whatever the origin, as long as the sequence is detectably present in a sample. While routine diagnostic tests may not be able to identify cancer cells in these samples, the method of the present invention identifies neoplastic cells derived from the primary tumor or from a metastases. The method includes non-invasive sampling (e.g., bodily fluid) as well as invasive sampling (e.g., biopsy). The sample of DNA of the subject may be serum, plasma, lymphocytes, urine, sputum, bile, stool, cervical tissue, saliva, tears, pancreatic juice, duodenal juice, cerebral spinal fluid, regional lymph node, histopathologic margins, and any bodily fluid that drains a body cavity or organ. Therefore, the method provides for the non-invasive detection of various tumor types including head and neck cancer, lung cancer, esophageal cancer, stomach cancer, small bowel cancer, colon cancer, bladder cancer, kidney cancers, cervical cancer and any other organ type that has a draining fluid accessible to analysis. For example, neoplasia of regional lymph nodes associated with a primary mammary tumor can be detected using the method of the invention. Regional lymph nodes for head and neck carcinomas include cervical lymph nodes, prelaryngeal lymph nodes, pulmonary juxta-esophageal lymph nodes and submandibular lymph nodes. Regional lymph nodes for mammary tissue carcinomas include the axillary and intercostal nodes. Samples also include urine DNA for bladder cancer or plasma or saliva DNA for head and neck cancer patients.

Any nucleic acid sample, in purified or nonpurified form, can be utilized as the starting nucleic acid or acids in accordance with the present invention, provided it contains, or is suspected of containing, a nucleic acid sequence containing a target locus (e.g., CpG-containing nucleic acid). In general, the CpG-containing nucleic acid is DNA. However, invention methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for detection of methylated CpG may be from any source including, but not limited to, brain, colon, urogenital, lung, renal, pancreas, liver, esophagus, stomach, hematopoietic, breast, thymus, testis, ovarian, and uterine tissue, and may be extracted by a variety of techniques such as that described by Maniatis, et al. (*Molecular Cloning: a Laboratory Manual*, Cold Spring Harbor, N.Y., pp 280, 281, 1982).

The nucleic acid of interest can be any nucleic acid where it is desirable to detect the presence of a differentially methylated CpG island. The CpG island comprises a CpG island located in a gene or regulatory region for a gene. A "CpG island" is a CpG rich region of a nucleic acid sequence. The nucleic acid sequence may include, for example, MICP 1–42. However, any gene or nucleic acid sequence of interest containing a CpG sequence can provide diagnostic information (i.e., via its methylation state) using invention methods.

Moreover, these markers can also be multiplexed in a single amplification reaction to generate a low cost, reliable cancer screening test for many cancers simultaneously.

A combination of DNA markers for CpG-rich regions of nucleic acid may be amplified in a single amplification reaction. The markers are multiplexed in a single amplification reaction, for example, by combining primers for more than one locus. For example, DNA from a urine sample can be amplified with three different randomly labeled primer sets, such as those used for the amplification of the MICP38–42 loci, in the same amplification reaction. The reaction products are separated on a denaturing polyacrylamide gel, for example, and then exposed to film for visualization and analysis. By analyzing a panel of markers, there is a greater probability of producing a more useful methylation profile for a subject.

If the sample is impure (e.g., plasma, serum, stool, ejaculate, sputum, saliva, cerebrospinal fluid, or blood or a sample embedded in paraffin), it may be treated before amplification with a reagent effective for lysing the cells contained in the fluids, tissues, or animal cell membranes of the sample, and for exposing the nucleic acid(s) contained therein. Methods for purifying or partially purifying nucleic acid from a sample are well known in the art (e.g., Sambrook et al., *Molecular Cloning: a Laboratory Manual*, Cold Spring Harbor Press, 1989, herein incorporated by reference).

In order to detect a differential methylation state for a gene or CpG-containing region of interest, invention methods include any means known in the art for detecting such differential methylation. For example, detecting the differential methylation may include contacting the nucleic acid-containing specimen with an agent that modifies unmethylated cytosine, amplifying a CpG-containing nucleic acid in the specimen by means of CpG-specific oligonucleotide primers, wherein the oligonucleotide primers distinguish between modified methylated and nonmethylated nucleic acid, and detecting the methylated nucleic acid based on the presence or absence of amplification products produced in said amplifying step. This embodiment includes the PCR-based methods described in U.S. Pat. No. 5,786,146, incorporated herein in its entirety.

For the first time, the methylation state of a number of genes has been correlated with cell proliferative disorders. Examples of such genesand their NCBI accession numbers, including the location of the clone, are set out in Table 1.

In another embodiment, detection of differential methylation is accomplished by contacting a nucleic acid sample suspected of comprising a CpG-containing nucleic acid with a methylation sensitive restriction endonuclease that cleaves only unmethylated CpG sites under conditions and for a time to allow cleavage of unmethylated nucleic acid. The sample is further contacted with an isoschizomer of the methylation sensitive restriction endonuclease, that cleaves both methylated and unmethylated CpG-sites, under conditions and for a time to allow cleavage of methylated nucleic acid. Oligonucleotides are added to the nucleic acid sample under conditions and for a time to allow ligation of the oligonucleotides to nucleic acid cleaved by the restriction endonuclease, and the digested nucleic acid is amplified by conventional methods such as PCR wherein primers complementary to the oligonucleotides are employed. Following identification, the methylated CpG-containing nucleic acid can be cloned, using method well known to one of skill in the art (see Sambrook et al., *Molecular Cloning: a Laboratory Manual*, Cold Spring; Harbor Press, 1989).

As used herein, a "methylation sensitive restriction endonuclease" is a restriction endonuclease that includes CG as part of its recognition site and has altered activity when the C is methylated as compared to when the C is not methylated. Preferably, the methylation sensitive restriction endonuclease has inhibited activity when the C is methylated (e.g., SmaI). Specific non-limiting examples of a methylation sensitive restriction endonucleases include Sma I, BssHII, or HpaII. Such enzymes can be used alone or in combination. Other methylation sensitive restriction endonucleases will be known to those of skill in the art and include, but are not limited to SacII, EagI, and BstUI, for example. An "isoschizomer" of a methylation sensitive restriction endonuclease is a restriction endonuclease which recognizes the same recognition site as a methylation sensitive restriction endonuclease but which cleaves both methylated and unmethylated CGs. One of skill in the art can readily determine appropriate conditions for a restriction endonuclease to cleave a nucleic acid (see Sambrook et al., *Molecular Cloning: a Laboratory Manual*, Cold Spring Harbor Press, 1989). Without being bound by theory, actively transcribed genes generally contain fewer methylated CGs than in other genes.

In one embodiment of the invention, a nucleic acid of interest is cleaved with a methylation sensitive endonuclease. In one aspect, cleavage with the methylation sensitive endonuclease creates a sufficient overhang on the nucleic acid of interest. Following cleavage with the isoschizomer, the cleavage product can still have a sufficient overhang. An "overhang" refers to nucleic acid having two strands wherein the strands end in such a manner that a few bases of one strand are not base paired to the other strand. A "sufficient overhang" refers to an overhang of sufficient length to allow specific hybridization of an oligonucleotide of interest. In one embodiment, a sufficient overhang is at least two bases in length. In another embodiment, the sufficient overhang is four or more bases in length. An overhang of a specific sequence on the nucleic acid of interest may be desired in order for an oligonucleotide of interest to hybridize. In this case, the isoschizomer can be used to create the overhang having the desired sequence on the nucleic acid of interest.

In another aspect of this embodiment, the cleavage with a methylation sensitive endonuclease results in a reaction product of the nucleic acid of interest that has a blunt end or an insufficient overhang. In this embodiment, an isoschizomer of the methylation sensitive restriction endonuclease can create a sufficient overhang on the nucleic acid of interest. "Blunt ends" refers to a flush ending of two stands, the sense stand and the antisense strand, of a nucleic acid.

Once a sufficient overhang is created on the nucleic acid of interest, an oligonucleotide is ligated to the nucleic acid cleaved of interest which has been cleaved by the methylation specific restriction endonuclease. "Ligation" is the attachment of two nucleic acid sequences by base pairing of substantially complementary sequences and/or by the formation of covalent bonds between two nucleic acid sequences. In one aspect of the present invention, an "oligonucleotide" is a nucleic acid sequence of about 2 up to about 40 bases in length. It is presently preferred that the oligonucleotide is from about 15 to 35 bases in length.

In one embodiment, an adaptor is utilized to create DNA ends of desired sequence and overhang. An "adaptor" is a double-stranded nucleic acid sequence with one end that has a sufficient single-stranded overhang at one or both ends such that the adaptor can be ligated by base-pairing to a sufficient overhang on a nucleic acid of interest that has been cleaved by a methylation sensitive restriction enzyme or an isoschizomer of a methylation sensitive restriction enzyme. Adaptors can be obtained commercially, or two oligonucleotides can be utilized to form an adaptor. Thus, in one embodiment, two oligonucleotides are used to form an adaptor; these oligonucleotides are substantially complementary over their entire sequence except for the region(s) at the 5' and/or 3' ends that will form a single stranded overhang. The single stranded overhang is complementary to an overhang on the nucleic acid cleaved by a methylation sensitive restriction enzyme or an isoschizomer of a methylation sensitive restriction enzyme, such that the overhang on the nucleic acid of interest will base pair with the 3' or 5' single stranded end of the adaptor under appropriate conditions. The conditions will vary depending on the sequence composition (GC vs AT), the length, and the type of nucleic acid (see Sambrook et al., *Molecular Cloning: a Laboratory Manual,* 2nd Ed.; Cold Spring Harbor Laboratory Press, Plainview, N.Y., 1998).

Following the ligation of the oligonucleotide, the nucleic acid of interest is amplified using a primer complementary to the oligonucleotide. Specifically, the term "primer" as used herein refers to a sequence comprising two or more deoxyribo-nucleotides or ribonucleotides, preferably more than three, and more preferably more than eight, wherein the sequence is capable of initiating synthesis of a primer extension product, which is substantially complementary to a nucleic acid such as an adaptor or a ligated oligonucleotide. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. In one embodiment, the primer is an oligodeoxyribo-nucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the oligonucleotide to be amplified and include the appropriate G or C nucleotides as discussed above. This means that the primers must be sufficiently complementary to hybridize with their respective strands under conditions which allow the agent for polymerization to perform. In other words, the primers should have sufficient complementarity with a 5' and 3' oligonucleotide to hybridize therewith and permit amplification of CpG containing nucleic acid sequence.

Primers of the invention are employed in the amplification process which is an enzymatic chain reaction that produces exponential quantities of target locus relative to the number of reaction steps involved (e.g., polymerase chain reaction or PCR). Typically, one primer is complementary to the negative (−) strand of the locus and the other is complementary to the positive (+) strand. Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphos-phoramidites are used as starting materials and may be synthesized as described by Beaucage,etal.(Tetrahedron Letters,22:1859–1862,1981). One method for synthesizing oligonucleotides on a modified solid support is described in U.S. Pat. No. 4,458,066.

Where the CpG-containing nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405–437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, generally at a pH of about 7–9. Preferably, a molar excess (for genomic nucleic acid, usually about 108:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. a large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to approximately room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation such as Taq DNA polymerase, and the like). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

Preferably, the method of amplifying is by PCR, as described herein and as is commonly used by those of ordinary skill in the art. However, alternative methods of amplification have been described and can also be employed. PCR techniques and many variations of PCR are known. Basic PCR techniques are described by Saiki et al. (1988 Science 239:487–491) and by U.S. Pat. Nos. 4,683, 195, 4,683,202 and 4,800,159, which are incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95.degree. C.) and incubation at a temperature permitting primer: adaptor hybridization and copying of the master-cut DNA fragment by the amplification enzyme. Heat stable amplification enzymes like the pwo, Thermus aquaticus or Thermococcus litoralis DNA polymerases are commercially available which eliminate the need to add enzyme after each denaturation cycle. The salt, cation, pH and related factors needed for enzymatic amplification activity are available from commercial manufacturers of amplification enzymes.

As provided herein an amplification enzyme is any enzyme which can be used for in vitro nucleic acid amplification, e.g. by the above-described procedures. Such amplification enzymes include pwo, Escherichia coli DNA polymerase I, Klenow fragment of E. coli DNA polymerase I, T4 DNA polymerase, T7 DNA polymerase, Thermus aquaticus (Taq) DNA polymerase, Thermococcus litoralis DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, E. coli DNA ligase or Q.beta. replicase. Preferred amplification enzymes are the pwo and Taq polymerases. The pwo enzyme is especially preferred because of its fidelity in replicating DNA.

Once amplified, the nucleic acid can be attached to a solid support, such as a membrane, and can be hybridized with any probe of interest, to detect any nucleic acid sequence. Several membranes are known to one of skill in the art for the adhesion of nucleic acid sequences. Specific non-limiting examples of these membranes include nitrocellulose (NITROPURE) or other membranes used in for detection of gene expression such as polyvinylchloride, diazotized paper and other commercially available membranes such as GENESCREEN, ZETAPROBE (Biorad), and NYTRAN Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

In one embodiment, representational difference analysis (RDA, see Lisitsyn et al., Science 259:946–951, 1993, herein incorporated by reference) can be performed on CpG-containing nucleic acid following MCA. MCA utilizes kinetic and subtractive enrichment to purify restriction endonuclease fragments present in one population of nucleic acid fragments but not in another. Thus, RDA enables the identification of small differences between the sequences of two nucleic acid populations. RDA uses nucleic acid from one population as a "tester" and nucleic acid from a second population as a "driver" in order to clone probes for single copy sequences present in (or absent from) one of the two populations. In one embodiment, nucleic acid from a "normal" individual or sample, not having a disorder such as a cell-proliferative disorder is used as a "driver," and nucleic acid from an "affected" individual or sample, having the disorder such as a cell proliferative disorder is used as a "tester." In one embodiment, the nucleic acid used as a "tester" is isolated from an individual having a cell proliferative disorder such as low grade astrocytoma, anaplastic astrocytoma, glioblastoma, medulloblastoma, gastric cancer, colorectal cancer, colorectal adenoma, acute myelogenous leukemia, leukemia, lung cancer, renal cancer, breast cancer, prostate cancer, endometrial cancer and neuroblastoma. The nucleic acid used as a "driver" is thus normal astrocytes, normal glial cells, normal brain cells, normal gastric cells, normal colorectal cells, normal leukocytes, normal lung cells, normal kidney cells, normal breast cells, normal prostate cells, normal uterine cells, and normal neurons, respectively. In an additional embodiment, the nucleic acid used as a "driver" is isolated from an individual having a cell proliferative disorder such as low grade astrocytoma, anaplastic astrocytoma, glioblastoma, medulloblastoma, gastric cancer, colorectal cancer, colorectal adenoma, acute myelogenous leukemia, leukemia, lung cancer, renal cancer, breast cancer, prostate cancer, endometrial cancer and neuroblastoma. The nucleic acid used as a "tester" is thus normal astrocytes, normal glial cells, normal brain cells, normal gastric cells, normal colorectal cells, normal leukocytes, normal lung cells, normal kidney cells, normal breast cells, normal prostate cells, normal uterine cells, and normal neurons, respectively. One of skill in the art will readily be able to identify the "tester" nucleic acid useful with to identify methylated nucleic acid sequences in given "driver" population.

The materials for use in the assay of the invention are ideally suited for the preparation of a kit. Therefore, in accordance with another embodiment of the present invention, there is provided a kit it useful for the detection of a cellular proliferative disorder in a subject having or at risk for said cellular proliferative disorder. Invention kits include a carrier means compartmentalized to receive a sample in close confinement therein, one or more containers comprising a first container containing a reagent which modifies unmethylated cytosine and a second container containing primers for amplification of a CpG-containing nucleic acid, wherein the primers distinguish between modified methylated and nonmethylated nucleic acid, and optionally, a third container containing a methylation sensitive restriction endonuclease. Primers contemplated for use in accordance with the invention include those that would amplify sequences or fragments thereof as set forth in SEQ ID NOs: 1–42.

Carrier means are suited for containing one or more container means such as vials, tubes, and the like, each of the container means comprising one of the separate elements to be used in the method. In view of the description provided herein of invention methods, those of skill in the art can readily determine the apportionment of the necessary reagents among the contaniner means. For example, one of the container means can comprise a container containing an oligonucleoltide for ligation to nucleic acid cleaved by a methylation sensitive restriction endonuclease. One or more container means can also be included comprising a primer complementary to the oligonucleotide. In addition, one or more container means can also be included which comprise a methylation sensitive restriction endonuclease. One or more container means can also be included containing an isoschizomer of said methylation sensitive restriction enzyme.

It should be noted that as used herein and in the appended claims, the singular forms "a," "and," and "the" include plural referents unless the context clearly dictates otherwise. Thus, for example, reference to "a cell" includes a plurality of such cells and reference to "the restriction enzyme" includes reference to one or more restriction enzymes and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following example is intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

Collection and Preparation of Pancreatic Cell Lines

The following pancreatic adenocarcinoma cell lines were used: PL3 and PL8 (both CIMP-cell lines (CpG island methylator phenotype) were from Dr. Elizabeth Jaffe, John Hopkins University); CAPAN1, CAPAN2, Panc1, Hs766T, and MiaPaca2 (from the American Type Culture Collection, Rockville, Md.) and Colo357 (from the European Collection of Animal Cell Cultures, Salisbury, United Kingdom). In addition, seventeen pancreatic cancer xenografts were selected at random from a total of 90 xenografts, which were established from the primary carcinomas as described in Ueki, et al., Cancer Res., 60:1835–1839, 2000. Forty-seven primary pancreatic adenocarcinomas, 15 normal pancreata, 5 pancreata from patients with chronic pancreatitis, and a panel of normal tissues were obtained from the resected surgical specimens at The Johns Hopkins Medical Institutions, Baltimore, Md. Frozen tissues or paraffin-embedded tissues were microdissected to obtain >40% neoplastic cellularity in the primary pancreatic adenocarcinomas, and 3 of the 15 frozen normal pancreatic tissues were also microdissected to enrich the normal ductal epithelium. DNA was extracted from microdissected primary pancreatic adenocarcinomas and normal tissues as well as from lymphocytes of four cancer-free individuals using standard methods.

EXAMPLE 2

Methylated CpG Island
Amplification/Representational Difference Analysis
(MCA/RDA)

MCA/RDA was performed as described by Toyota et al., Cancer Res., 59:2307–2312, 1999, modifying such procedure to increase the efficiency by digesting 5 μg of DNA with SmaI and XmaI (New England Biolabs). The restriction fragments were then ligated to RMCA adapter and amplified by PCR in 10 mM Tris-HCl (pH 8.3), 1.5 mM MgCl2, 50 mM KCl, 0.5 M betaine, 2% DMSO, 200 μM each deoxynucleotide triphosphate, 100 pmol of RMCA 24mer primer and 15 units of Taq polymerase (Life Technologies, Inc.) in a final reaction volume of 100 μl. The reaction mixture was then incubated at 72° C. for 5 min and at 95° C. for 3 min, and then subjected to 25 cycles of 1 min at 95° C. and 3 min at 77° C. followed by a final extension of 10 min at 77° C. Betaine was included in the PCR reaction to help amplify the methylated templates at a higher annealing temperature (77° C.). The combination of betaine and DMSO can uniformly amplify a mixture of DNA with different GC content (Baskaran, et al., Genome Res. 6:633–638, 1996). These modifications might have enhanced the amplification of distinct MICPs (methylated in carcinoma of the pancreas) instead of Alu repetitive sequences that accounted for 60% of the recovered clones using the original protocol (Toyota et al., Cancer Res. 59:2307–2312, 1999). The MCA amplicon from either the pancreatic cancer cell line PL3 or PL8 was used as the tester for RDA, and a MCA amplicon generated from a mixture of DNA from the normal pancreata of six different patients was used as the driver. RDA was performed on these MCA amplicons using different adapters, JMCA and NMCA. Sequences of adapters used for MCA/RDA are listed in Table 3A and 3B and are available at http://pathology2.jhu.edu/pancreas/prim0425.htm, which website is incorporated herein by reference. After the third round of competitive hybridization and selective amplification, the RDA difference products of second and third round amplifications were cloned into pBluescript II plasmid vector (Stratagene).

EXAMPLE 3

DNA Sequencing of Clones and Dot Blot Hybridization

The clones recovered from each cell line after MCA/RDA were amplified with T3 and T7 primers and then sequenced using KS primer as recommended by the manufacturer (Sequitherm Excel; Epicentre Technologies). To determine the methylation status of MCA/RDA MICPs in pancreatic cancer and normal pancreas, MICPs were screened by hybridizing them to a dot blot of MCA products of pancreatic cancers and normal pancreata. Plasmid DNA containing each independent clone was prepared and digested with SmaI. DNA fragments were recovered from agarose gel and used as a probe for dot blot hybridization. Aliquots (1 μl) of the mixture of 10×SSC and MCA products from the driver and from the tester (PL3 and PL8) both before and after each of the three rounds of RDA competitive hybridization/selective amplification were blotted onto nylon membranes in duplicate. Similarly, MCA products from six pancreatic cell lines (CAPAN1, CAPAN2, Panc1, Hs766T, MiaPaca2, and Colo357) and from eight other normal pancreata were also blotted onto the membranes. The membranes were hybridized with 32P-labeled probes overnight, washed, and exposed to a Kodak X-ray film.

EXAMPLE 4

Bisulfite Modification, Bisulfite-Modified Genomic Sequencing, and Methylation-Specific PCR (MSP)

The bisulfite treatment was carried out for 16 h at 50° C. using 1 μg of genomic DNA, as described in Ueki, et al., Cancer Res., 60:1835–1839, 2000. Genomic sequencing was performed on bisulfite-treated DNA to examine the methylation status of 10–20 CpG dinucleotides located in and/or around SmaI sites of each clone in 22 pancreatic tissues (8 cancer cell lines, 6 primary adenocarcinomas, and 8 normal pancreata; Ueki, et al., Cancer Res. 60:1835–1839, 2000). Genomic sequencing of the coding sequence of cyclin G was also performed in PL8. The level of methylation of each clone was determined by quantifying the level of methylation of each CpG site by comparing the intensity of unconverted cytosine with that of cytosine plus thymidine. Generally, in pancreatic cancer cell lines, the level of methylation observed at each CpG dinucleotide was consistent throughout the CpG island. Therefore, the average level of methylation of each sequence was graded and placed into one of 4 grades: 0–10%, 11–30%, 31–70%, and 71–100%. MSP was performed as described in Herman, et al., Proc. Natl. Acad. Sci. USA 93:9821–9826, 1996, and to acquire optimal specificity, each primer pair contained four to six CpG sites, and high specific annealing temperatures were used. The primers and the specific annealing temperatures for each clone are listed in Table 3 and are available at http://pathology2.jhu.edu/pancreas/prim0425.htm, which website is incorporated herein by reference. If validated MSP primers sets specific for methylated and unmethylated templates revealed that there was only amplification of methylated templates, the samples are presumed to be 100% methylated. Methylated and unmethylated templates were identified by bisulfite-modified sequencing. In describing MSP results performed on CpG islands that were normally unmethylated in non-neoplastic pancreas, a cancer sample was termed "methylated" if MSP yielded any methylated templates.

EXAMPLE 5

Reverse Transcription-PCR (RT-PCR) and 5-aza-2'-deoxycytidine (5Aza-dC) Treatment Five pancreatic cancer cell lines (PL3, PL8, CAPAN2, Panc1, and MiaPaca2) and four normal pancreata were used for RT-PCR analysis. The cell lines were treated with demethylating agent 5Aza-dC (Sigma Chemical Co.) at a final concentration of 1 μM for 5 days. Total RNA was prepared using TRIzol (Life Technologies, Inc.), reverse-transcribed and amplified. As a control for cDNA integrity, glyceraldehyde-3-phosphate dehydrogenase gene (GAPDH) was also amplified. Primer sequences for RT-PCR are listed in Table 3 and are available at http://pathology2.jhu.edu/pancreas/prim0425.htm, which website is incorporated herein by reference.

EXAMPLE 6

Statistics

The primary outcome variable was the observed number of 7 MICP loci found to be methylated in 64 pancreatic cancers. Wilcoxon's rank-sum test compared the observed number of methylated loci by tumor differentiation (poorly versus well or moderately differentiated), lymph node status (0 or 1 versus >1 node positive), and prior CIMP classification (CIMP positive versus CIMP negative). Simple linear regression assessed the relationship between the observed number of methylated loci and these covariates: age, age squared, and tumor diameter (in cm). Multivariate linear regression assessed the simultaneous contribution of the clinicopathological and demographic variables to the observed number of methylated loci. All of the tests were two-sided. A P of <0.05 signified statistical significance.

EXAMPLE 7

Patient Population and Tissue Samples

Normal and tumor specimens were obtained from pancreatic adenocarcinomas resected at The Johns Hopkins Hospital. Pancreatic cancer xenografts were established from the primary carcinomas as previously described in Caldas, et al., Nature Genet. 8:27–31, 1994, and carcinoma and normal tissues were stored at −70° C. Thirty-two xenografts were selected at random. Three MSI carcinoma xenografts were added, as reported previously, as well as another MSI primary carcinoma (Goggins, et al., Am. J. of Pathology 152: 1501–1507, 1998). Genomic DNA was prepared from 35 xenografts and 9 pancreatic adenocarcinoma cell lines (BxPc3, Capan1, Capan2, Panc1, CFPAC1, MiaPaca2, Hs766T (all from ATCC, Rockville, Md.), Co10357 (from ECACC, Salisbury, UK) and PL45, a low passage cell line established in the Goggin Laboratory at John Hopkins University School of Medicine). Where available, DNA was obtained from primary pancreatic cancer tissue frozen at −80 C. since Whipple resection. Frozen tissues were microdissected to obtain DNA from normal pancreatic tissue and the pancreatic carcinoma.

Patient records were reviewed to determine a history of cigarette smoking, diabetes mellitus, and prognosis, and a family history of pancreatic cancer. These data were reviewed in the context of the DNA methylation data.

EXAMPLE 8

Bisulfite Modification and Genomic Sequencing

The bisulfite treatment was carried out for 16 h at 56° C. on 1 µg of genomic DNA, according to the procedure of Herman et al, Proc. Natl. Acad. Sci. USA 93:9821–9826, 1996. Modified DNA was purified and eluted into 50 µl of LoTE buffer. The primers used for genomic sequencing of bisulfite-treated DNA are listed in Table 3 and are available at http://pathology2.jhu.edu/pancreas/prim0425.htm, which website is incorporated herein by reference. PCR was performed on 1–2 µl of bisulfite-treated DNA, and prior to sequencing, PCR reactions were incubated with exonuclease I and shrimp alkaline phosphatase (Amersham, according to the manufacturer recommendations). Sequencing of PCR products was performed in microtiter plates as recommended by the manufacturer (Sequitherm Excel, Epicentre Technologies, Madison, Wis.).

EXAMPLE 9

Methylation-Specific PCR (MSP) Assay

The methylation status of each gene was determined by MSP as described by Herman et al, Proc. Natl. Acad. Sci. USA 93:9821–9826, 1996, in which the sequence difference of bisulfite-treated DNA was detected by PCR using primers specific for either the methylated or for the unmethylated DNA. Primer sequences and the specific annealing temperatures for 13 genes are listed in Table 3 and are available at http://pathology2.jhu.edu/pancreas/prim0425.htm, which website is incorporated herein by reference. MSP was performed on 1 µl of bisulfite-treated DNA under the conditions as follows: 95° C. for 3 min; then 35–40 cycles of 95° C. for 30s, the specific annealing temperature for 30s, and 72° C. for 30s; and a final extension of 4 min at 72° C. Five µl of each PCR product were directly loaded onto 3% agarose gels or 10% acrylamide gels, stained with ethidium bromide and visualized under UV illumination. All PCR reactions were performed with positive controls for both unmethylated and methylated alleles, and no DNA control. Finally, 3–6 CpG sites were included in each primer pair and the specific annealing temperatures were used for each gene to obtain optimal specificity.

EXAMPLE 10

Identification of Differentially Methylated Sequences

Figure 2:
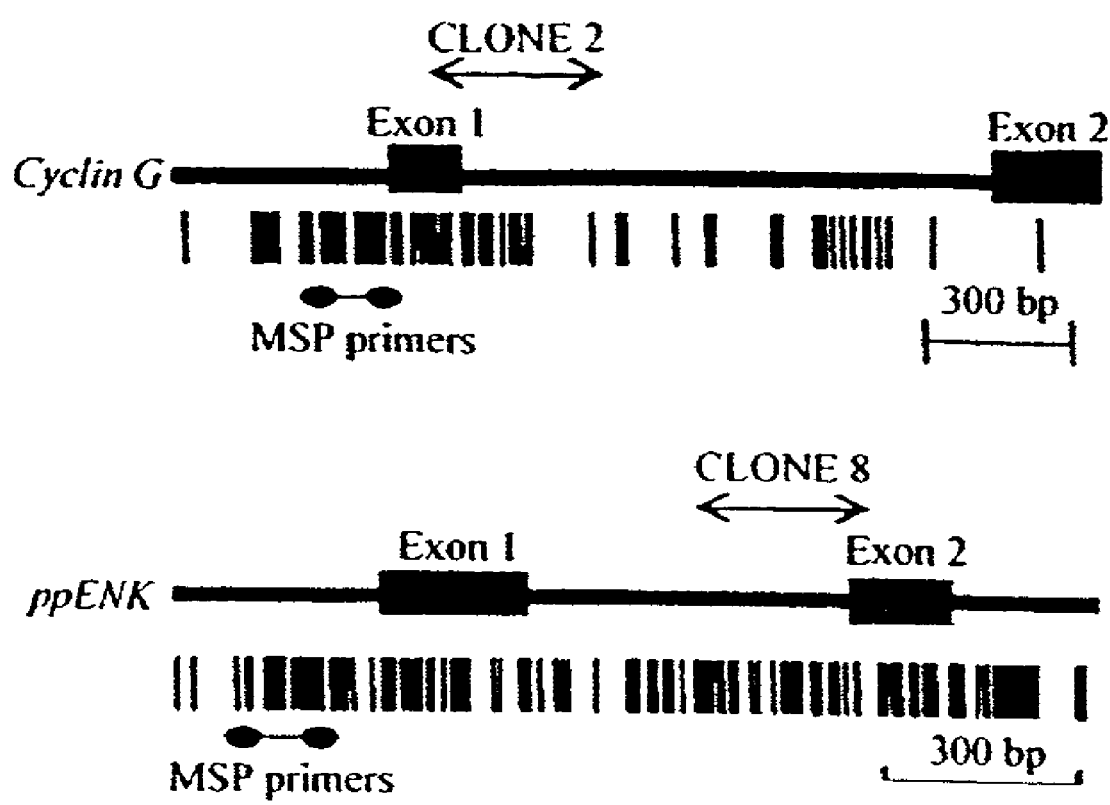
FIG. 2 shows a CpG plot across the 5' CpG islands of Cyclin G and ppENK showing the relation between isolated clones and their corresponding genes. The positions of MSP primers are also indicated. The black boxes represent exons.

The strategy of MCA/RDA has been previously reported (Toyota, et al., Cancer Res. 59:2307–2312, 1997). Ninety-six randomly selected clones recovered from each cell line were subjected to DNA sequencing and 66 clones were revealed to be independent. Only 3 clones contained Alu-repetitive sequences. The subsequent probing of labeled clones to MCA products of tester and driver by dot-blot hybridization revealed that 43 of 66 clones (MICP1–43) were differentially methylated in the tester compared to the driver (FIG. 1). These 43 clones were also variably methylated in the other 6 pancreatic cancer cell lines examined. A description of these 43 differentially methylated clones is shown in Table 1. All of the 43 clones had a GC content of greater than 50% and 41 (95%) had a sequence uniqueness sustaining the criteria of CpG island (Gardiner-Garden & Frommer, J. Mol. biol. 196:261–282, 1987). The DNA homology search of each clone with the BLAST program (National Center for Biotechnology Information) demonstrated that 84% (36) of the 43 clones had significant homologies to known human sequences, including 8 clones matched to human gene sequences and 9 clones matched to human ESTs. Five clones were also matched or contained a part of CpG islands isolated previously (Toyota, et al., Cancer Res. 59:2307–2312, 1997, Cross, et al., Nat. Genet., 6:236–244, 1994) and 14 clones had significant homology to High-Throughput Genome Sequences in the three International Nucleotide Sequence databases: DDBJ, EMBL and GenBank. The remaining 7 had no significant homology to known sequences. MICP1 corresponded to the 3' noncoding region of the human homeobox gene CSX, MICP2 corresponded to exon 1 and intron 1 of the human Cyclin G, MICP3 corresponded to 5' region of the human endothelin-converting enzyme-like 1 gene ECEL1, MICP4 corresponded to intron 1 of the human glutamate decarboxylase 1 gene GAD1, MICP5 corresponded to exon 7 to exon 9 of the human ICAM5, MICP6 corresponded to intron 2 to intron 3 of the human monocarboxylate transporter 3 gene MCT3, MICP7 corresponded to the 5' region of the human B-cell specific transcriptional factor gene PAX5, MICP8 corresponded to intron 1 and exon 2 of the human Preproenkephalin gene (ppENK) (FIG. 2). Interestingly, 3 clones (MICP1, 17 and 22) matched to CpG islands originally recovered from colorectal cancer cell line using the same technique (named MINT 23, 20 and 32, respectively) (Toyota, et al., Cancer Res. 59:2307–2312, 1997).

EXAMPLE 11

Characterization of the Sequences

Figure 4:
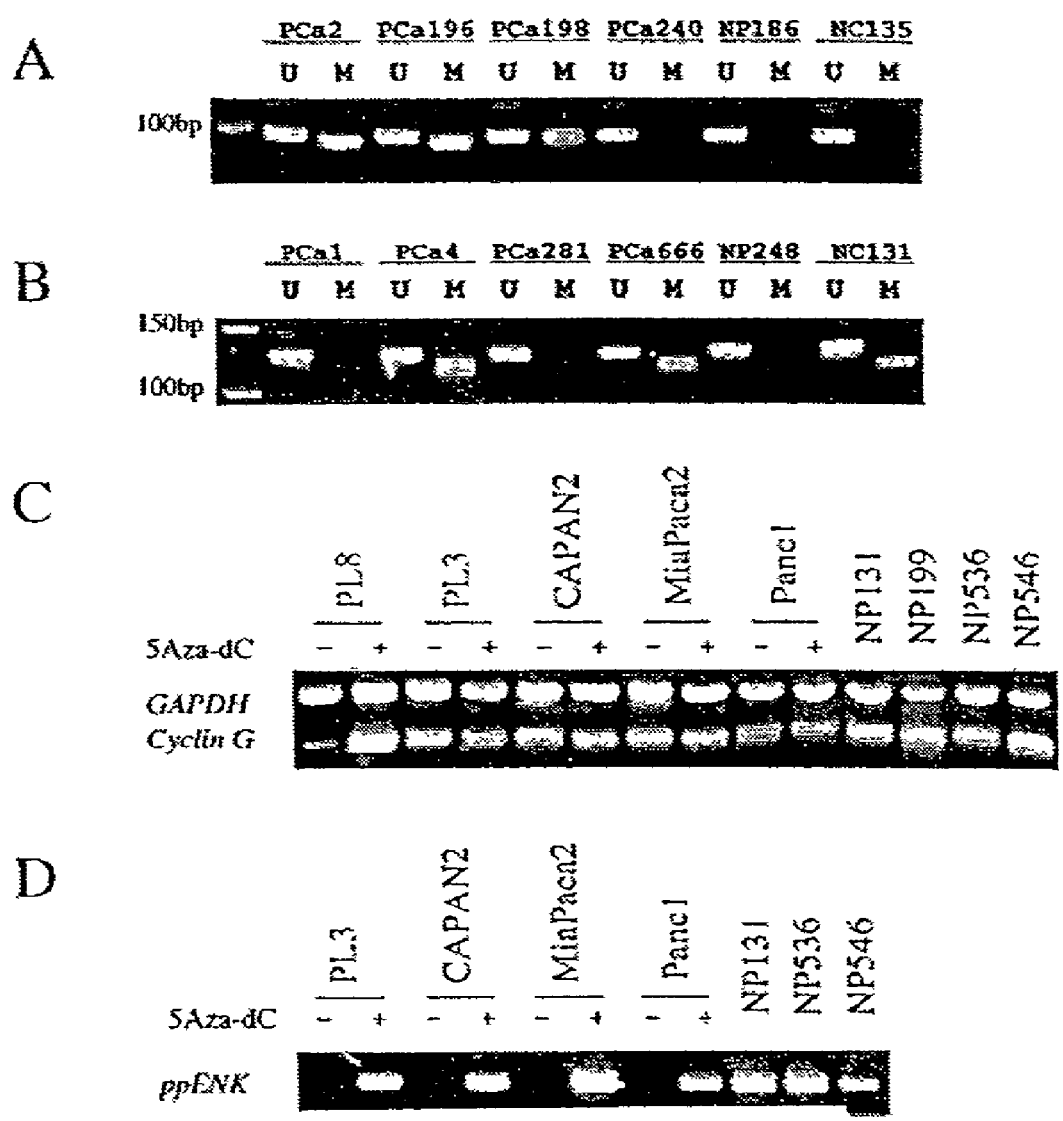
FIG. 4 shows MSP analyses of MICP36 (A) and MICP25 (B) in primary pancreatic adenocarcinomas and normal tissues. The PCR products in the lanes U and M indicate the presence of unmethylated and methylated templates, respectively. PCa, primary pancreatic carcinoma, NP, normal pancreas, NC, normal colonic mucosa. Expression of Cyclin G (C) and ppENK (D) in pancreatic cancer cell lines and normal pancreata by RT-PCR analysis. Cyclin G and ppENK were coamplified with GAPDH to ensure the RNA integrity. Cyclin G was expressed at low level in the methylated cell line PL8 compared with unmethylated cell lines (PL3, CAPAN2, MiaPaca2, and Panc1) and four normal pancreata. 5 Aza-dC treatment increased Cyclin G expression in PL8. All methylated cell lines examined (PL3, CAPAN2, MiaPaca2 and Panc1) lacked expression of ppENK, whereas all three normal pancreata expressed ppENK. Treatment of four cell lines with 5 Aza-dC restored the ppENK expression. The expected sizes of the PCR products are 306 bp for GAPDH, 207 bp for Cyclin G, and 179 bp for ppENK.

For 30 of the 43 clones, methylation was detected in 2 or more out of 8 normal pancreata by dot blot analysis, suggesting that these clones could be frequently methylated in normal pancreas. Therefore, only the remaining 13 clones were further analyzed by bisulfite sequencing. For seven of the clones (Cyclin G, ppENK, MICP20, 23, 33, 35 and 36), methylation was restricted to pancreatic cancers (FIG. 4A and 4B). In the case of 5 clones (MCT3, PAX5, MICP15, 16 and 38), methylation was detectable in DNA from normal pancreata as well as DNA from cancer tissues (FIG. 3C). In the thirteenth clone (MICP42), cytosines at CpG sites were similarly methylated in both pancreatic cancers and normal pancreata. The sequence uniqueness of this clone also did not satisfy the criteria for CpG islands. A summary of the level of methylation of each clone is shown in FIG. 3D. There was little individual variation in the level of methylation of these 6 clones (MCT3, PAX5, MICP15, 16, 38 and 42) in normal pancreata from 8 patients at the age from 34 to 84 years old (FIG. 3 and data not shown). Interestingly, the methylation of these CpG islands in normal pancreata was sometimes heterogeneous. For example, although the SmaI site of MICP15 was not methylated in normal pancreata, 2 CpG sites near the SmaI site were methylated (FIG. 3C). A summary of the results of MCA/RDA and bisulfite sequencing is also provided in FIG. 4.

Figure 5:
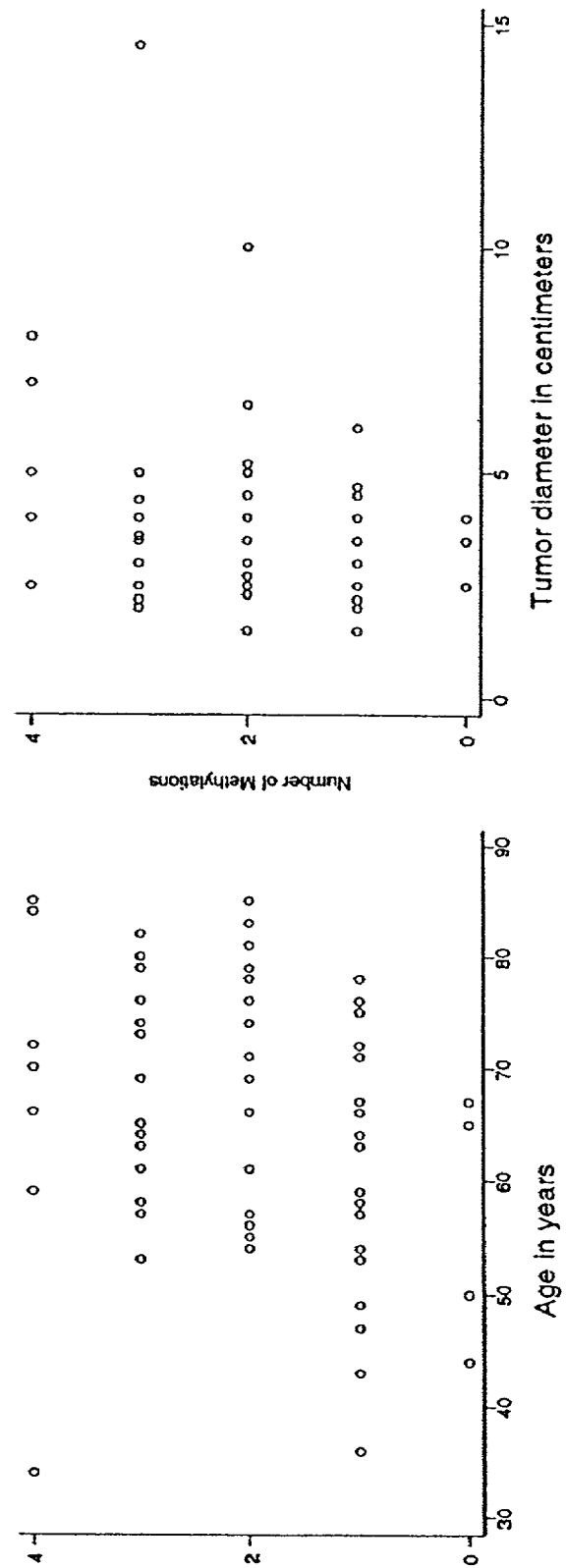
FIG. 5 shows aberrant methylation of MICPs and clinicopathological variables. Multivariate linear regression analysis was used to determine the relationship between the number of aberrantly methylated MICPs in a pancreatic adenocarcinoma and the variables patient age (left plot) and tumor diameter (right plot). For each decade increase in age, the average number of methylated loci increases by 0.28, regardless of the tumor diameter. For each increase in tumor diameter (in cm), the number of mehtylated loci increases by 0.156 regardless of patient age.

In order to identify low level of methylation of identified clones in pancreatic tissues, MSP primers were designed for the 7 clones (Cyclin G, ppENK, MICP20, 23, 33, 35 and 36) differentially methylated in pancreatic cancers by bisulfite sequencing. The methylation status of these clones was examined in 15 primary pancreatic adenocarcinomas, 5 DNA samples from pancreata with chronic pancreatitis as well as 14 normal pancreata including three specimens enriched in normal ductal epithelium. For MICP36, MSP detected methylation in DNA of three pancreatic cancer cell lines but not in any other specimens examined. Aberrant methylation of the remaining 6 clones was detected in 7% to 87% of primary pancreatic adenocarcinomas, while MSP confirmed a lack of methylation of these 6 clones in DNA from 14 normal pancreata (FIG. 5 and Table 2A and 2B). DNA from one chronic pancreatitis tissue containing pancreatic intraductal neoplasia (PanIN) (Hruban, et al., Clin. Cancer Res. 6:2969–2972, 2000) harbored methylated templates of Cyclin G, ppENK and MICP20 and DNA from another chronic pancreatitis sample also had methylated templates of ppENK.

Because tissue-specific methylation differences can be found in normal tissues (Liang, et al., Genomics 53:260–268, 1998), the clones found that were aberrantly methylated in pancreatic cancer, as compared to normal pancreas, were also analyzed to see if they are methylated in other normal tissues. By MSP, MICPs 33 and 35 were not methylated in any normal gastrointestinal tissues, while ppENK, MICP20 and 23 were methylated in DNA samples from normal gastric, duodenal and colonic mucosae (FIG. 5 and Table 2A and 2B). Amplification of methylated templates of these clones was always weak in normal mucosae compared to the primary pancreatic adenocarcinomas (FIG. 3), suggesting that there were few methylated DNA templates in these mucosae.

EXAMPLE 12

Expression of Cyclin G and ppENK in Pancreatic Cancer

To determine whether methylation of these clones resulted in loss or decrease of gene expression, Cyclin G and ppENK were further examined using RT-PCR in 5 and 4 pancreatic cell lines, respectively. Partial methylation (~50%) of the 5' CpG island of Cyclin G in PL8 (FIG. 4C) was associated with decreased expression of Cyclin G by RT-PCR. The 5' CpG island of Cyclin G was not methylated in a panel of normal pancreata. Cyclin G was expressed in 4 normal pancreata by RT-PCFR. Treatment with 5Aza-dC restored the expression of Cyclin G in PL8 (FIG. 4C). Using RT-PCR, it was found that ppENK was expressed in normal pancreata but not in any of the 4 pancreatic cancer cell lines examined in which 5' CpG island of this gene was methylated. 5Aza-dC treatment restored ppENK expression in all 4 cell lines (FIG. 4D). Thus, hypermethylation of the 5' CpG islands of Cyclin G and ppENK is coincides with decreased expression in pancreatic cancers.

EXAMPLE 13

Determination of Methylated ppENK by Methylation Specific PCR of Pancreatic Fluid as a Specific Marker of Pancreatic Cancer Pancreatic fluid obtained from patients undergoing pancreatic surgical resection from 38 patients with pancreatic cancer, 7 with chronic pancreatitis, 4 with miscellaneous tumors (islet cell, serous cyst adenoma, and lymphoma), 9 with ampullary cancers, 9 with IPMNs (intraductal papillary mucinous neoplasms) and 3 from bile duct cancers was analyzed. Methylated ppENK was detected in 55% of pancreatic cancer fluids, none in the chronic pancreatitis or other miscellaneous tumor group, 2 of 9 with IPMN, 2 of 3 with bile duct cancer, and 4 of 9 with ampullary cancer, suggesting that the specificity of methylated ppENK in pancreatic fluid is useful as a diagnostic marker.

Although the invention has been described with reference to the presently preferred embodiment, it should be understood that various modifications can be made without departing from the spirit of the invention. Accordingly, the invention is limited only by the following claims.

TABLE 1A

The 42 MICPs identified by MCA/RDA in pancreatic cancers*

| MICP | Blast homology | Size (bp) | CpG Islands** | Chromosome |
|---|---|---|---|---|
| 1 | CSX | 414 | yes | 5q35 |
| 2 | Cydin G | 392 | yes | 5q32–34 |
| 3 | FLJ00083 | 479 | no | not known |
| 4 | GADI | 309 | yes | 2 |
| 5 | HLH | 179 | yes | 20 |
| 6 | ICAM5 | 630 | yes | 19p13.2 |
| 7 | MCT3 | 308 | yes | 22q12.3–q31.2 |
| 8 | PAX5 | 548 | yes | 9p13 |
| 9 | ppENK | 255 | yes | 8q23–q24 |
| 10 | SMO | 229 | yes | 7q34–q36 |
| 11 | ZBP | 399 | yes | 5q22 |
| 12 | Human EST | 431 | yes | Xp22 |
| 13 | Human EST | 600 | yes | 3p |
| 14 | Human EST | 510 | yes | 5 |
| 15 | Human EST | 359 | yes | not known |
| 16 | Human EST | 370 | yes | 12q |
| 17 | Human EST | 324 | yes | 6q |
| 18 | Human EST | 415 | yes | 11q |
| 19 | Human EST | 392 | yes | not known |
| 20 | Human EST | 359 | yes | 11q14 |
| 21 | Human EST | 545 | yes | 19q13.3 |
| 22 | Human CpG island | 386 | yes | 7q34–q36 |
| 23 | Human CpG island | 464 | yes | 20q13 |
| 24 | Human CpG island | 526 | yes | 15 |
| 25 | Human CpG island | 280 | yes | 6p22.1–23 |
| 26 | Human CpG island | 422 | yes | 1 |
| 27 | Human geriomic DNA | 257 | yes | 17 |
| 28 | Human genomic DNA | 350 | yes | 7q34–q36 |
| 29 | Human genormc DNA | 336 | yes | 10 |

TABLE 1A-continued

The 42 MICPs identified by MCA/RDA in pancreatic cancers*

| MICP | Blast homology | Size (bp) | CpG Islands** | Chromosome |
|---|---|---|---|---|
| 30 | Human genomic DNA | 293 | yes | 2q36–q37 |
| 31 | Human genomic DNA | 427 | yes | 13 |
| 32 | Human genomic DNA | 470 | no | 21q22.3 |
| 33 | Human genomic DNA | 264 | yes | Xq22.1–23 |
| 34 | Human genomic DNA | 371 | yes | 20p11.21–11.23 |
| 35 | Human genomic DNA | 445 | yes | 4 |
| 36 | Human genomic DNA | 357 | yes | 19q13.1 |
| 37 | Human genomic DNA | 312 | yes | 7p14–15 |
| 38 | Human genomic DNA | 372 | yes | 5 |
| 39 | No homology | 307 | yes | not known |
| 40 | No homology | 331 | yes | not known |
| 41 | No homology | 304 | yes | not known |
| 42 | No homology | 307 | yes | not known |

*7 of these 42 MICPs were methylated in pancreatic cancer and not normal pancreas (see text)
**minimal length, 200 Bp; GC content, >50%; CpG/GpC. >0.5(11)

TABLE 1B

| MICP* | Size | % GC | CpG/GpC | CpG Islands? | NCBI Acc. #** | Location of clone*** |
|---|---|---|---|---|---|---|
| 1 | 414 | 64.3 | 0.811 | yes | AF135523 | 1–414 |
| 2 | 392 | 62.8 | 0.613 | yes | D86077 | 35–426 |
| 3 | 479 | 63.9 | 0.444 | no | AK024484 | 1645–2107 |
| 4 | 309 | 64.4 | 0.727 | yes | AC007405 | 72554–72862 |
| 5 | 179 | 68.3 | 1.330 | yes | AL121673 | 66270–66448 |
| 6 | 630 | 65.6 | 0.625 | yes | AF082802 | 5502–6131 |
| 7 | 308 | 66.6 | 0.704 | yes | AF132611 | 1082–1389 |
| 8 | 548 | 60.4 | 0.683 | yes | AL161781 | 129660–130226 |
| 9 | 255 | 67.8 | 0.867 | yes | V00509 | 622–876 |
| 10 | 229 | 58.2 | 0.927 | yes | AC083866 | 37615–37843 |
| 11 | 399 | 59.1 | 0.800 | yes | AC016663 | 106325–106723 |
| 12 | 431 | 68.4 | 0.909 | yes | AC002365 | 159360–159790 |
| 13 | 600 | 65.5 | 0.661 | yes | AC024167 | 62307–62906 |
| 14 | 510 | 63.7 | 0.771 | yes | AF135520 | 1–510 |
| 15 | 359 | 65.5 | 0.972 | yes | AW028607 | 259–376 |
| 16 | 370 | 64.9 | 1.030 | yes | AC026335 | 11182–11568 |
| 17 | 324 | 67.6 | 0.816 | yes | AC068247 | 66045–66347 |
| 18 | 415 | 61.9 | 0.767 | yes | AP002781 | 190243–190537 |
| 19 | 392 | 55.1 | 1.214 | yes | AI557774 | 193–392 |
| 20 | 359 | 55.6 | 0.731 | yes | AP002354 | 58648–59006 |
| 21 | 545 | 65.0 | 1.023 | yes | AC007785 | 13354–13898 |
| 22 | 386 | 66.3 | 0.605 | yes | AC005998 | 48200–48585 |
| 23 | 464 | 65.7 | 0.975 | yes | AF135532 | 1–464 |
| 24 | 526 | 64.2 | 0.645 | yes | AC074201 | 59279–59804 |
| 25 | 280 | 68.1 | 0.929 | yes | AL136305 | 115130–115409 |
| 26 | 422 | 63.0 | 0.767 | yes | AL137797.1 | 38754–39186 |
| 27 | 257 | 65.8 | 0.852 | yes | AC004706 | 88868–89124 |
| 28 | 350 | 64.9 | 0.900 | yes | AC004897 | 60876–611125 |
| 29 | 336 | 64.4 | 0.606 | yes | AC005661 | 43755–44090 |
| 30 | 293 | 67.0 | 0.760 | yes | AC012033 | 113181–113473 |
| 31 | 427 | 66.7 | 0.884 | yes | AC013721 | 31973–32339 |
| 32 | 470 | 59.6 | 0.292 | no | AJ239326 | 83971–84440 |
| 33 | 264 | 63.3 | 0.580 | yes | AL035088 | 102596–102859 |
| 34 | 371 | 63.0 | 0.722 | yes | AL080312 | 56645–57015 |
| 35 | 445 | 64.0 | 0.884 | yes | AC023868 | 130032–030491 |
| 36 | 357 | 68.9 | 0.800 | yes | AC002133 | 31977–32333 |
| 37 | 312 | 67.5 | 0.885 | yes | AC005826 | 151694–152005 |
| 38 | 372 | 65.6 | 0.778 | yes | AC011376 | 56983–57313 |
| 39 | 307 | 68.7 | 0.844 | yes | no homology | |
| 40 | 331 | 70.7 | 0.707 | yes | no homology | |
| 41 | 304 | 68.8 | 0.794 | yes | no homology | |
| 42 | 307 | 68.7 | 0.875 | yes | no homology | |

*Total 4 clones with no homology to known human sequences (MICP38–42) and 38 clones matched t⑦
11 clones matched to the human genes (MICP1–11)
10 clones matched to human ESTs (MICP12–21)

TABLE 2A

| Sample | age | Tumor Diam. (cm) | nodes | no. methylated | ppENK | MIC27 | MICP38 | MICP25 | MICP36 | CyclinG | zbp |
|---|---|---|---|---|---|---|---|---|---|---|---|
| AsPC1 | | | | 3 | | | | | | | |
| BxPC3 | | | | 3 | | | | | | | |
| CAPAN1 | | | | 3 | | | | | | | |
| CAPAN2 | | | | 3 | | | | | | | |
| CFPAC | | | | 2 | | | | | | | |
| Colo357 | | | | 5 | | | | | | | |
| Hs76ST | | | | 3 | | | | | | | |
| MIaPaca2 | | | | 4 | | | | | | | |
| Panc1 | | | | 2 | | | | | | | |
| PL3 | | | | 5 | | | | | | | |
| PL8 | | | | 4 | | | | | | | |
| Px17 | 69 | 4.4 | + | 2 | | | | | | | |
| Px29 | 66 | 2.5 | + | 3 | | | | | | | |
| Px30 | 57 | 3.0 | + | 0 | | | | | | | |
| Px64 | 76 | 2.5 | + | 1 | | | | | | | |
| Px65 | 63 | 2.2 | + | 1 | | | | | | | |
| Px74 | 83 | 3.5 | + | 2 | | | | | | | |
| Px75 | 63 | 5.0 | 0 | 2 | | | | | | | |
| Px76 | 64 | 2.2 | + | 3 | | | | | | | |
| Px102 | 47 | 3.0 | 0 | 1 | | | | | | | |
| Px108 | 76 | 3.0 | + | 2 | | | | | | | |
| Px120 | 70 | 5.0 | + | 4 | | | | | | | |
| Px132 | 61 | 3.6 | + | 3 | | | | | | | |
| (x143 | 54 | 2.0 | + | 1 | | | | | | | |
| Px184 | 59 | 4.0 | + | 4 | | | | | | | |
| Px186 | 55 | 4.0 | + | 2 | | | | | | | |
| Px195 | 67 | 4.0 | + | 0 | | | | | | | |
| Px282 | 79 | 3.0 | 0 | 2 | | | | | | | |
| 1 | 64 | 4.7 | 0 | 1 | | | | | | | |
| 2 | 57 | 3.0 | + | 2 | | | | | | | |
| 4 | 54 | 2.7 | + | 2 | | | | | | | |
| 6 | 69 | 4.5 | + | 2 | | | | | | | |
| 9 | 85 | 8.0 | + | 4 | | | | | | | |
| 11 | 65 | 2.5 | + | 0 | | | | | | | |
| 12 | 81 | 10.0 | + | 2 | | | | | | | |
| 13 | 53 | | + | 1 | | | | | | | |
| 14 | 57 | 3.0 | + | 2 | | | | | | | |
| 195 | 84 | 5.0 | + | 4 | | | | | | | |
| 198 | 76 | 4.0 | + | 3 | | | | | | | |
| 240 | 50 | 3.5 | 0 | 0 | | | | | | | |
| 248 | 67 | 2.0 | + | 1 | | | | | | | |
| 281 | 36 | 6.0 | + | 1 | | | | | | | |
| 287 | 72 | 2.5 | 0 | 1 | | | | | | | |
| 666 | 34 | 8.0 | + | 4 | | | | | | | |
| 5350 | 44 | 4.0 | + | 0 | | | | | | | |
| 11632 | 66 | 6.5 | + | 2 | | | | | | | |
| 12616 | 58 | 8x | | 1 | | | | | | | |
| 13671 | 58 | 6.0 | + | 1 | | | | | | | |
| 13653 | 63 | 14.5 | + | 3 | | | | | | | |
| 17496 | 73 | 3.5 | + | 3 | | | | | | | |
| 20852 | 78 | 5.0 | + | 2 | | | | | | | |
| 21190 | 82 | 3.5 | + | 3 | | | | | | | |
| 21889 | 80 | 4.0 | + | 3 | | | | | | | |
| 22384 | 74 | 2.0 | + | 3 | | | | | | | |

TABLE 2A-continued

| | | | | | | | | | | | |
|---|---|---|---|---|---|---|---|---|---|---|---|
| 24494 | 78 | 3.5 | + | 1 | | | | | | | |
| 24721 | 71 | 2.5 | + | 2 | | | | | | | |
| 25392 | 57 | 3.0 | + | 1 | | | | | | | |
| 25183 | 56 | 1.5 | 0 | 2 | | | | | | | |
| 30011 | 65 | 4.0 | + | 3 | | | | | | | |
| 30845 | 76 | 2.5 | + | 3 | | | | | | | |
| 31742 | 66 | 1.5 | 0 | 1 | | | | | | | |
| 32006 | 61 | | 0 | 2 | | | | | | | |
| 35083 | 59 | 1.5 | + | 1 | | | | | | | |
| 35583 | 75 | 3.0 | + | 1 | | | | | | | |
| 36378 | 74 | 5.2 | + | 2 | | | | | | | |
| 37880 | 43 | 4.0 | 0 | 1 | | | | | | | |
| 42946 | 71 | 3.5 | + | 2 | | | | | | | |
| 45885 | 53 | 8x | | 3 | | | | | | | |
| 46391 | 79 | 2.3 | + | 2 | | | | | | | |
| 49126 | 49 | 4.0 | + | 1 | | | | | | | |
| 49390 | 79 | 2.5 | + | 3 | | | | | | | |
| 52150 | 72 | 7.0 | 0 | 3 | | | | | | | |
| 52226 | 58 | 3.5 | + | 3 | | | | | | | |
| 53413 | 85 | 3.5 | + | 2 | | | | | | | |
| 55090 | 71 | 4.5 | + | 1 | | | | | | | |

TABLE 2B

Results of MSP

| | n* | CLONE 2 Cyclin G | CLONE 8 PPENK | CLONE 20 | CLONE 23 | CLONE 33 | CLONE 35 | CLONE 36 |
|---|---|---|---|---|---|---|---|---|
| Primary pancreatic carcinoma | 15 | 7% | 87% | 13% | 53% | 33% | 40% | 0% |
| Normal pancreata | 14 | 0% | 0% | 0% | 0% | 0% | 0% | 0% |
| Chronic pancreatitis | 5 | 20% | 40% | 20% | 0% | 0% | 0% | ND |
| Normal gastirc mucoase | 6 | ND | ND | 50% | 17% | 0% | 0% | ND |
| Normal duodenal mucoase | 8 | ND | 100%** | 50% | 75% | 0% | 0% | ND |
| Normal colonic mucoase | 6 | ND | 100%*** | 33% | 100% | 0% | 0% | ND |
| Normal lymphocytes | 4 | 0% | 0% | 0% | 0% | 0% | 0% | ND |

*number examined
**only 4 samples examined
***only 3 samples examined

TABLE 3A

PRIMER SEQUENCE FOR BISIULFITE-SEQUENCE

| Clone | Orientation | Sequence | Annealing Temperature | SEQ ID NO: |
|---|---|---|---|---|
| RARβ | Forward | 5'-GAGTTGGTGATGTTAGATTAG-3' | | 43 |
| | Reverse | 5'-TTCCCAAAAAAATCCCAAATTC-3' | 56 | 44 |
| | Sequence | 5'-CTCCTTCCAAATAAATACTTAC-3' | | 45 |
| THBS1 | Forward | 5'-AGAGAGGAGTTTAGATTGG-3' | | 46 |
| | Reverse | 5'-CAAAAAAACTAAAACCTCAAC-3' | 54 | 47 |
| | Sequence | Forward primer | | |
| CACNA1G | Forward | 5'-TGGATAAAGGATGTTTGGGGTTTG-3' | 55, 53, 51, | 48 |
| | Reverse | 5'-CCCTCCCCTTACCCCTAAATCC-3' | 49* | 49 |
| | Sequence | 5'-ACTCCCCCTCACTTTATTC-3' | | 50 |
| hMLH1 | Forward | 5'-ATTATTTTAGTAGAGGTATATAAG-3' | 58 | 51 |
| | Reverse | 5'-CCAACCCCACCCTTCAAC-3' | | 52 |
| | Sequence | Forward primer | | |
| MINT1 | Forward | 5'-AAGAGAGGGTTGGAGAGTAG-3' | 62 | 53 |
| | Reverse | 5'-CCCCTAAAAAAAAAATCAAAAATC-3' | | 54 |
| | Sequence | 5'-GGGTTGGAGAGTAGGGGAGTT-3' | | 55 |

TABLE 3A-continued

PRIMER SEQUENCE FOR BISIULFITE-SEQUENCE

| Clone | Orientation | Sequence | Annealing Temperature | SEQ ID NO: |
|---|---|---|---|---|
| MINT2 | Forward | 5'-YGTTATGATTTTTTTGTTTAGTTAAT-3' | 60, 58, 56, 54** | 56 |
| | Reverse | 5'-TACACCAACTACCCAACTACCTC-3' | | 57 |
| | Sequence | 5'-ACTTCCATTAAAAACAACTAC-3' | | 106 |
| MINT31 | Forward | 5'-TTTATTTATATAATTTTGTGTATGG-3' | 58 | 58 |
| | Reverse | 5'-CACCCCTCACTTTACTAAAAC-3' | | 59 |
| | Sequence | Reverse primer | | |
| MINT32 | Forward | 5'-TTTGGGAGGTAAATTYGTTGATT-3' | 58, 56, 54, 52*** | 60 |
| | Reverse | 5'-ACCRAACAAAAAACCTAAAAAAAC-3' | | 61 |
| | Sequence | Forward primer | | |

*55 (5 cycles), 53 (5 cycles), 51 (5 cycles), 49 (26 cycles)
**60 (3 cycles), 58 (4 cycles), 56 (5 cycles), 54 (26 cycles)
***58 (3 cycles), 56 (4 cycles), 54 (5 cycles), 52 (26 cycles)

TABLE 3B

PRIMER SEQUENCES FOR MSP

| Clone | Orientation & Methylation | Sequence | Annealing Temperature | SEQ ID NO: |
|---|---|---|---|---|
| P16 | Unmethylated | F 5'-TTATTAGAGGGTGGGGTGGATTGT-3' | 60 | 62 |
| | | R 5'-CAACCCCAAACCCACAACCATAA-3' | | 107 |
| | Methylated | F 5'-TTATTAGAGGGTGGGGCGGATCGC-3' | 65 | 63 |
| | | R 5'-GACCCCCGAACCGCGACCCTAA-3' | | 108 |
| RARβ | Unmethylated | F 5'-AGGATTGGGATGTTGAGAATG-3' | 58 | 64 |
| | | R 5'-TTACAAAAAAACCTTCCAAATACA-3' | | 109 |
| | Methylated | F 5'-GGATTGGGATGTCGAGAAC-3' | 64 | 65 |
| | | R 5'-TACAAAAAACCTTCCGAATACG-3' | | 110 |
| CACNA1G | Unmethylated | F 5'-GTTTTTTTTTGGATTTTTGTTTTTTG-3' | 60 | 66 |
| | | R 5'-TTTATTCCAACTTCTTCACTTCA-3' | | 111 |
| | Methylated | F 5'-GTTTTTTCGGGGCGGTTTC-3' | 62 | 67 |
| | | R 5'-TTCCGACTTCTTCGCTTCG-3' | | 112 |
| TIMP-3 | Unmethylated | F 5'-TTTTGTTTTGTTATTTTTGTTTTTGGTTTT-3 | 59 | 68 |
| | | R 5'-CCCCCCAAAAACCCCACCTCA-3' | 59 | 69 |
| | Methylated | F 5'-CGTTTCGTTATTTTTTGTTTTCGGTTTTC-3' | | 113 |
| | | R 5'-CCGAAAACCCCGCCTCG-3' | | 114 |
| THBS1 | Unmethylated | F 5'-GTTTGGTTGTTGTTTATTGGTTG-3' | 62 | 70 |
| | | R 5'-CCTAAACTCACAAACCAACTCA-3' | | 71 |
| | Methylated | F 5'-TGCGAGCGTTTTTTTAAATGC-3' | 62 | 72 |
| | | R 5'-TAAACTCGCAAACCAACTCG-3' | | 73 |
| HMLH1 | Unmethylated | F 5'-TTAATAGGAAGAGTGGATAGTG-3' | 56 | 74 |
| | | R 5'-TCTATAAATTACTAAATCTCTTCA-3' | | 75 |
| | Methylated | F 5'-TTAATAGGAAGAGCGGATAGC-3' | 58 | 76 |
| | | R 3'-CTATAAATTACTAAATCTCTTCG-3' | | 77 |

TABLE 3B-continued

PRIMER SEQUENCES FOR MSP

| Clone | Orientation & Methylation | Sequence | Annealing Temperature | SEQ ID NO: |
|---|---|---|---|---|
| E-Cad | Unmethylated | F 5'-TAATTTTAGGTTAGAGGGTTATTGT-3' | 53 | 78 |
| | | R 5'-CACAACCAATCAACAACACA-3' | | 79 |
| | Methylated | F 5'-TTAGGTTAGAGGGTTATCGCGT-3' | 57 | 80 |
| | | R 5'-TAACTAAAAATTCACCTACCGAC-3' | | 81 |
| DAPK | Unmethylated | F 5'-GGAGGATAGTTGGATTGAGTTAATGTT-3' | 60 | 82 |
| | | R 5'-CAAATCCCTCCCAAACACCAA-3' | | 83 |
| | Methylated | F 5'-GGATAGTCGGATCGAGTTAACGTC-3' | 60 | 84 |
| | | R 5'-CCCTCCCAAACGCCGA-3' | | 85 |
| MGMT | Unmethylated | F 5'-TTTGTGTTTTGATGTTTGTAGGTTTTTGT-3' | 59 | 86 |
| | | R 5'-AACTCCACACTCTTCCAAAAACAAACA-3' | | 87 |
| | Methylated | F 5'-TTTCGACGTTCGTACCTTTTCGC-3' | 59 | 88 |
| | | R 5'-GCACTCTTCCGAAAACGAAACG-3' | | 89 |
| MINT1 | Unmethylated | F 5'-GGGGTTGAGGTTTTTTGTTAGT-3' | 64 | 90 |
| | | R 5'-TTCACAACCTCAAATCTACTTCA-3' | | 91 |
| | Methylated | F 5'-GGGTTGAGGTTTTTTGTTAGC-3' | 64 | 92 |
| | | R 5'-CTACTTCGCCTAACCTAACG-3' | | 93 |
| MINT2 | Unmethylated | F 5'-GGTGTTGTTAAATGTAAATAATTTG-3' | 58 | 94 |
| | | R 5'-AAAAAAAAACACCTAAAACTCA-3' | | 95 |
| | Methylated | F 5'-AATCGAATTTGTCGTCGTTTC-3' | 60 | 96 |
| | | R 5'-AAATAAATAAATAAAAAAAAACGCG-3' | | 97 |
| MINT31 | Unmethylated | F 5'-GAATTGAGATGATTTTAATTTTTGT-3' | 64 | 98 |
| | | R 5'-CTAAAACCATCACCCCTAAACA-3' | | 99 |
| | Methylated | F 5'-TTGAGACGATTTTAATTTTTGC-3' | 62 | 100 |
| | | R 5'-AAAACCATCACCCCTAAACG-3' | | 101 |
| MINT32 | Unmethylated | F 5'-GAGTGGTTAGAGGAATTTAGGT-3' | 62 | 102 |
| | | R 5'-CTAAAAAAACAAACAAAACATCCA-3' | | 103 |
| | Methylated | F 5'-GTGGTTAGAGGAATTTAGGC-3' | 64 | 104 |
| | | R 5'-AAAACGAACGAAACGTCCG-3' | | 105 |

What is claimed is:

1. A method for detecting in a subject a cellular proliferative disorder associated with pancreatic cancer or colorectal cancer, comprising:
   a) contacting a nucleic acid-containing specimen from the subject with an agent that provides a determination of the methylation state of a preproenkephalin (ppENK) gene; and
   b) identifying aberrant methylation of regions of the gene or regulatory region, wherein aberrant methylation is identified as being different when compared to the same regions of the gene or associated regulatory region in a subject not having said cellular proliferative disorder, thereby detecting in the subject a cellular proliferative disorder associated with pancreatic cancer or colorectal cancer;
wherein aberrant methylation comprises hypermethylation when compared to the same regions of the gene or associated regulatory regions in a subject not having the cellular proliferative disorder.

2. The method of claim 1, wherein the regions of said gene are contained within CpG rich regions.

3. The method of claim 1, wherein the regions comprise regulatory regions of the gene.

4. The method of claim 1, wherein the agent is a pair of primers that hybridize with a target sequence in the gene or associated regulatory region of the gene.

5. The method of claim 1, wherein the nucleic acid-containing specimen comprises colonic tissue or pancreatic tissue.

6. The method of claim 1, wherein the nucleic acid-containing specimen is selected from the group consisting of serum, urine, blood, duodenal fluid, pancreatic fluid, ascites fluid, stool, and biopsy sample.

7. The method of claim 1, wherein the cellular proliferative disorder is pancreatic cancer.

* * * * *